(12) United States Patent
Hosogoe

(10) Patent No.: US 11,986,152 B2
(45) Date of Patent: May 21, 2024

(54) ENDOSCOPE CAP, ENDOSCOPE AND METHOD OF MANUFACTURING ENDOSCOPE CAP

(71) Applicant: HOYA CORPORATION, Tokyo (JP)

(72) Inventor: Yoshitsugu Hosogoe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 17/717,468

(22) Filed: Apr. 11, 2022

(65) Prior Publication Data

US 2022/0233058 A1 Jul. 28, 2022

Related U.S. Application Data

(63) Continuation of application No. 15/568,748, filed as application No. PCT/JP2017/025966 on Jul. 18, 2017, now abandoned.

(30) Foreign Application Priority Data

Jul. 19, 2016 (JP) ................................. 2016-141763
Jul. 19, 2016 (JP) ................................. 2016-141764

(51) Int. Cl.
*A61B 1/00* (2006.01)
*A61B 1/005* (2006.01)
(Continued)

(52) U.S. Cl.
CPC ............ *A61B 1/00098* (2013.01); *A61B 1/00* (2013.01); *A61B 1/00137* (2013.01);
(Continued)

(58) Field of Classification Search
CPC ..................................... A61B 1/00098–00101
See application file for complete search history.

(56) References Cited

U.S. PATENT DOCUMENTS 5,562,600 A 10/1996 Matsuno
5,569,157 A * 10/1996 Nakazawa .......... A61B 1/00177
600/106
(Continued)

FOREIGN PATENT DOCUMENTS

CN 101073492 A 11/2007
JP H05-076479 A 3/1993
(Continued)

OTHER PUBLICATIONS

U.S. Appl. No. 15/568,748, "Advisory Action", Jun. 14, 2021, 4 pages.
(Continued)

*Primary Examiner* — Alexandra L Newton
(74) *Attorney, Agent, or Firm* — Kilpatrick Townsend & Stockton LLP

(57) ABSTRACT

Provided is an endoscope cap or the like with an elevator which is easily attached to and detached from the distal end of an endoscope.
An endoscope cap attachable to and detachable from an endoscope including a lever pivotally provided at a distal end of an insertion part of an endoscope and a pivot part causing the lever to pivot comprises: a cylindrical cover; and an elevator which is pivotally supported at the inside of the cover, is connected to the lever when the endoscope is attached to the cover, and pivots in response to pivoting of the lever.

5 Claims, 37 Drawing Sheets

(51) Int. Cl.
*A61B 1/018* (2006.01)
*G02B 23/24* (2006.01)

(52) U.S. Cl.
CPC ............ *A61B 1/0057* (2013.01); *A61B 1/018* (2013.01); *G02B 23/24* (2013.01)

(56) References Cited

U.S. PATENT DOCUMENTS

| | | | |
|---|---|---|---|
| 5,674,181 | A | 10/1997 | Iida |
| 2007/0270638 | A1 | 11/2007 | Kitano et al. |
| 2016/0089004 | A1 | 3/2016 | Morimoto |
| 2018/0249894 | A1 | 9/2018 | Kolberg et al. |

FOREIGN PATENT DOCUMENTS

| | | |
|---|---|---|
| JP | H06-315458 A | 11/1994 |
| JP | H07-111967 A | 5/1995 |
| JP | H08-056900 A | 3/1996 |
| JP | H08-182648 A | 7/1996 |
| JP | 2002017655 A | 1/2002 |
| JP | 2006020725 A | 1/2006 |
| JP | 2006075238 A | 3/2006 |
| JP | 2016067771 A | 5/2016 |

OTHER PUBLICATIONS

U.S. Appl. No. 15/568,748, "Final Office Action", Apr. 8, 2021, 8 pages.
U.S. Appl. No. 15/568,748, "Final Office Action", Jan. 11, 2022, 9 pages.
U.S. Appl. No. 15/568,748, "Non-Final Office Action", Sep. 20, 2021, 6 pages.
U.S. Appl. No. 15/568,748, "Non-Final Office Action", Jan. 15, 2021, 7 pages.
CN201780001258.5, "Office Action", Jan. 28, 2019, 9 pages.
JP2018-039973, "Office Action", Feb. 12, 2019, 2 pages.
JP2018-039973, "Reconsideration Report", Nov. 15, 2019, 2 pages.

* cited by examiner

ENDOSCOPE CAP, ENDOSCOPE AND METHOD OF MANUFACTURING ENDOSCOPE CAP

CROSS-REFERENCE TO RELATED APPLICATIONS

This application is a continuation of U.S. application Ser. No. 15/568,748, filed Oct. 25, 2017, which is the national phase under 35 U. S. C. § 371 of PCT International Application No. PCT/JP2017/025966, filed Jul. 18, 2017, which claims priority to Japanese Patent Application No. 2016-141763, filed Jul. 19, 2016, and to Japanese Patent Application No. 2016-141764, filed Jul. 19, 2016, the contents of which are incorporated by reference.

FIELD

The present invention relates to an endoscope cap, an endoscope and a method of manufacturing an endoscope cap.

BACKGROUND

An endoscope having an elevator at the distal end of a channel passing through the inside of an insertion part has been used. The elevator is used to bend a treatment tool or the like inserted into the channel and to guide the tool to have a desired orientation.

An endoscope provided with a wall between an elevator and an elevating wire which moves the elevator is disclosed in Japanese Patent Application Laid-Open Publication No. H8-56900 (hereinafter, referred to as Patent Document 1). An endoscope having an elevator mounted to a cap which is detachable from the distal end of an insertion part is disclosed in Japanese Patent Application Laid-Open Publication No. 2002-17655 (hereinafter, referred to as Patent Document 2).

An endoscope in which an elevator, an elevating wire and a cap covering the elevator are detachable from an insertion part is disclosed in Japanese Patent Application Laid-Open Publication No. H6-315458 (hereinafter, referred to as Patent Document 3).

SUMMARY

The endoscope disclosed in Patent Document 1 takes a lot of work in cleaning because of its complicated structure around the elevator. The endoscopes disclosed in Patent Documents 2 and 3 require a lot of trouble in attachment and detachment of the cap.

According to an aspect, an object is to provide an endoscope cap with an elevator which is easily attached to and detached from the distal end of an endoscope.

An endoscope cap attachable to and detachable from an endoscope including a lever pivotally provided at a distal end of an insertion part of the endoscope and a pivot part causing the lever to pivot, comprises: a bottomed cylindrical cover that has an opening end that is attachable to and detachable from the distal end of the insertion part of the endoscope; a pedestal that is fixed to an inner side of the cover and that has an elevator attachment hole; and an elevator that is located at the inner side of the cover, and that has an elevator shaft inserted into the elevator attachment hole, an elevating part protruding in a direction intersecting the elevator shaft and a connection concave part opened at the opening end side of the elevating part and connected to the lever, the elevator being able to pivot around the elevator shaft with respect to the pedestal.

According to an aspect, an endoscope cap with an elevator which is easily attached to and detached from the distal end of the endoscope may be provided.

The above and further objects and features will more fully be apparent from the following detailed description with accompanying drawings.

DETAILED DESCRIPTION

Embodiment 1

Figure 1:
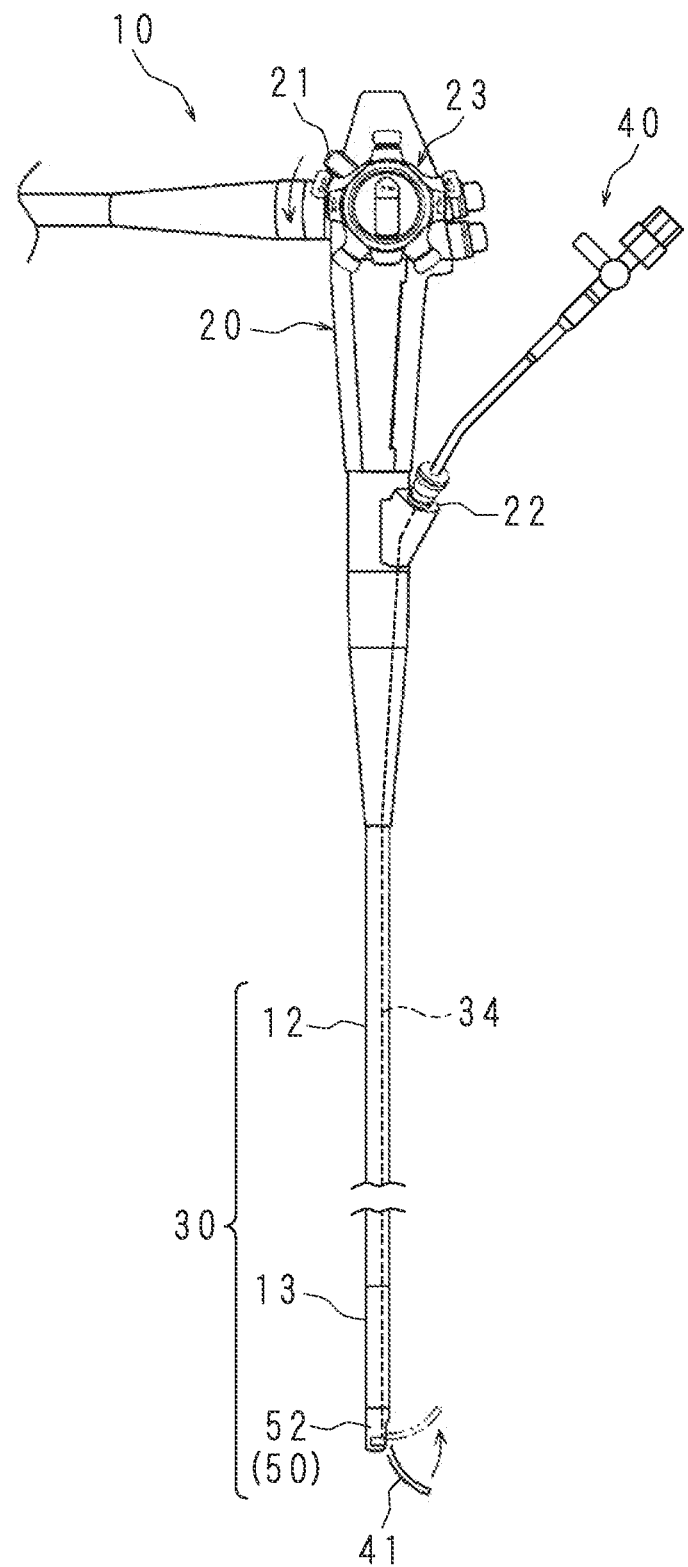
FIG. 1 illustrates an outer appearance of an endoscope.

FIG. 1 illustrates the outer appearance of an endoscope 10. The endoscope 10 according to the present embodiment is a flexible endoscope directed to an upper gastrointestinal tract. The endoscope 10 has an operation part 20 and an insertion part 30.

The operation part 20 includes an elevator operation lever 21, a channel inlet 22 and a bending knob 23. The operation part 20 is connected to a video processor, a light source device, a display device and so forth that are not illustrated.

The insertion part 30 is long and has one end connected to the operation part 20. The insertion part 30 has, from the operation part 20 side, a flexible section 12, a bending section 13 and a cap 50. The flexible section 12 is flexible. The bending section 13 bends in response to the operation of the bending knob 23. The cap 50 covers a rigid distal end portion 31 (see FIG. 2) that is contiguous from the bending section 13. The cap 50 is an example of an endoscope cap according to the present embodiment.

In the endoscope 10 according to the present embodiment, the cap 50 may be attached or detached to/from the distal end portion 31. The cap 50 has a cover 52 which is an exterior member and an elevator 80 (see FIG. 2). The detailed structure of the cap 50 will be described later.

In the following description, the longitudinal direction of the insertion part 30 will be referred to as an insertion direction. Likewise, along the insertion direction, the side closer to the operation part 20 will be referred to as a proximal side, whereas the side farther from the operation part 20 will be referred to as a distal side.

Figure 2:
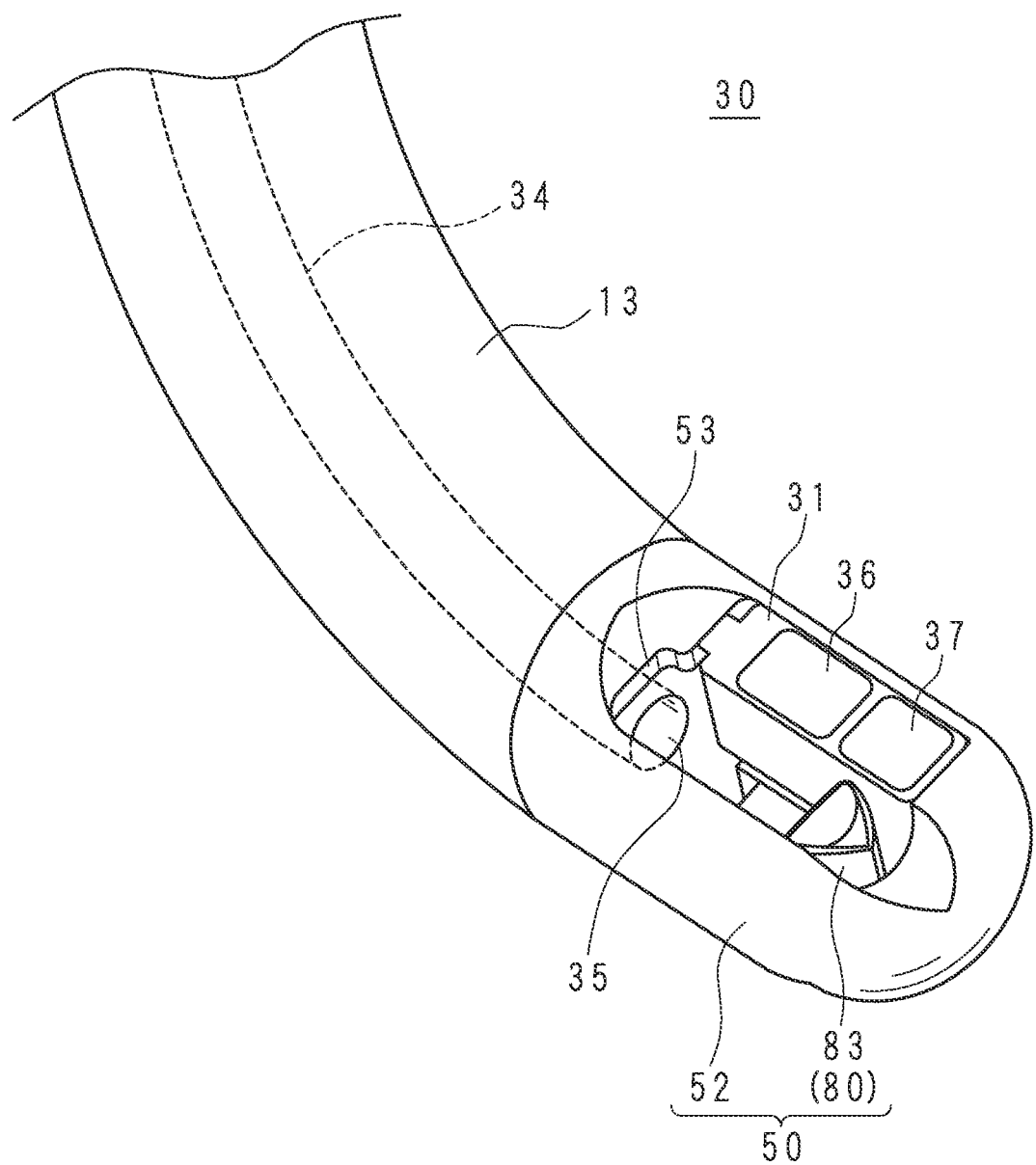
FIG. 2 is a perspective view of a distal end of an insertion part.
Figure 3:
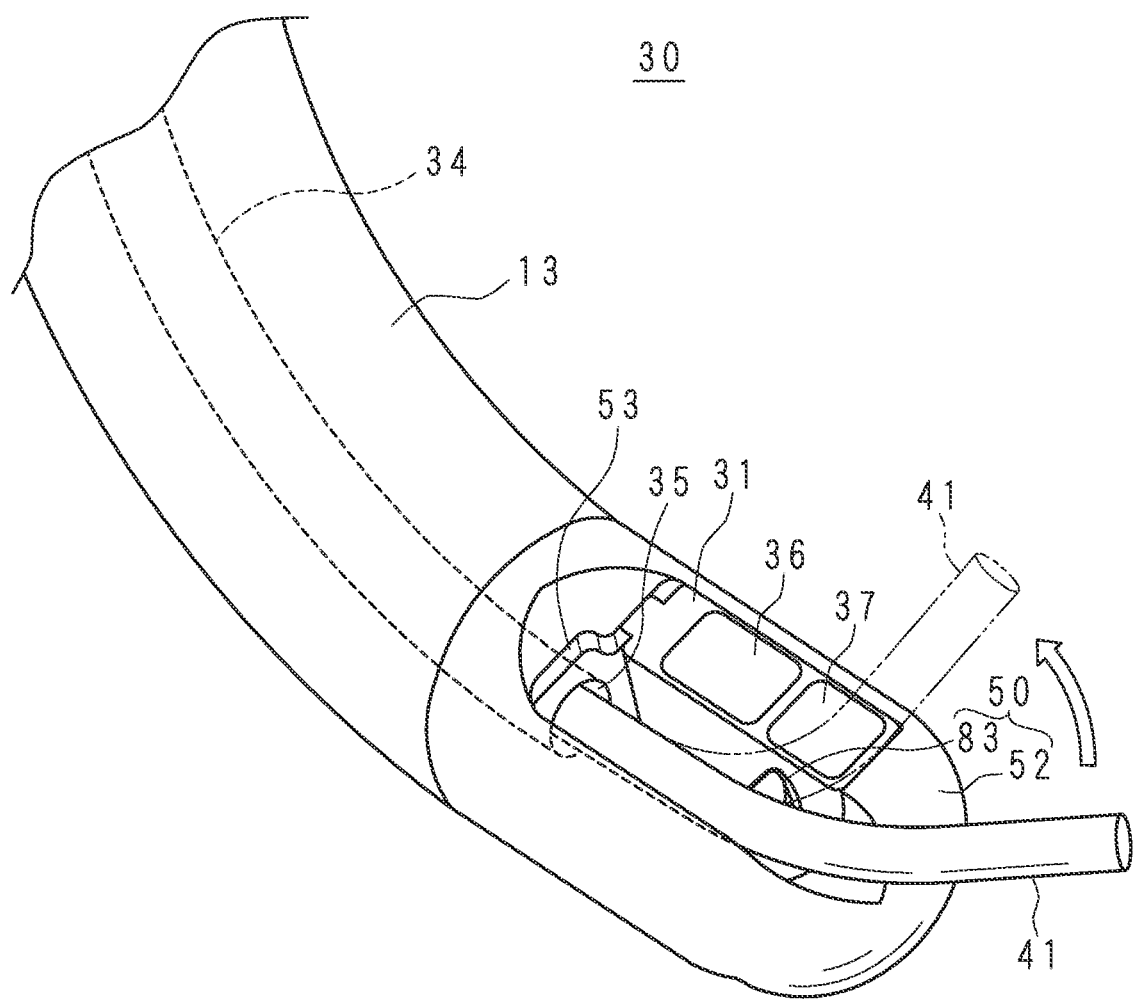
FIG. 3 illustrates a state where a treatment tool tip end protrudes from the distal end of the insertion part.

FIG. 2 is a perspective view of a distal end of the insertion part 30. FIG. 3 illustrates the state where a treatment tool tip end 41 protrudes from the distal end of the insertion part 30. The configuration of the endoscope 10 according to the present embodiment will be described with reference to FIGS. 1 to 3.

A distal end portion 31 located at the distal end of the bending section 13 has, on one side thereof, an observation window 36 and an illumination window 37 that are aligned on one side along the insertion direction. The illumination window 37 is located more toward the distal side than the observation window 36. The distal end portion 31 has a channel outlet 35 at the proximal side on the other side thereof. An elevating part 83 is disposed at the distal side of the channel outlet 35. The cover 52 which covers the distal end portion 31 has a substantially rectangular window part 53 at a portion corresponding to the observation window 36, illumination window 37 and elevating part 83.

The illumination window 37 directs the illumination light emitted from a light source device (not illustrated). Through the observation window 36, it is possible to optically observe the area irradiated with the illumination light. The endoscope 10 according to the present embodiment is of a so-called side view type, in which a viewing direction for optical observation is a direction intersecting the insertion direction. The endoscope 10 may also be of a forward oblique view type with a viewing direction somewhat inclined toward the distal end or a backward oblique view type with a viewing direction somewhat inclined toward the proximal end.

The channel inlet 22 and the channel outlet 35 are connected with each other by a channel 34 running through the inner side of the flexible section 12 and the bending section 13. The treatment tool 40 may be inserted through the channel inlet 22 from the treatment tool tip end 41, to protrude the treatment tool tip end 41 from the channel outlet 35.

As illustrated by the solid line in FIG. 3, the treatment tool tip end 41 protrudes while curving gently over the elevating part 83. If the elevator operation lever 21 is operated as illustrated by the arrow in FIG. 1, a lever 60 moves as described later, and an elevator 80 also moves in conjunction with the lever 60. As the elevator 80 moves, the treatment tool tip end 41 located over the elevator 80 is bent toward the proximal side, i.e. the operation part 20 side, as indicated by the arrows in FIGS. 1 and 3. The movement of the treatment tool tip end 41 is photographed by an image sensor (not illustrated) or the like through the observation window 36, and is displayed on a display device (not illustrated).

The treatment tool 40 is an instrument for treatment, for example, a high-frequency knife, forceps or contrast tube. The instrument to be inserted into the channel 34 is not limited to the instrument for treatment. For example, an instrument for observation such as an ultrasound probe or ultra-slim endoscope may also be inserted into the channel 34 and used. In the following description, the treatment tool 40 includes an instrument for observation.

Figure 4:
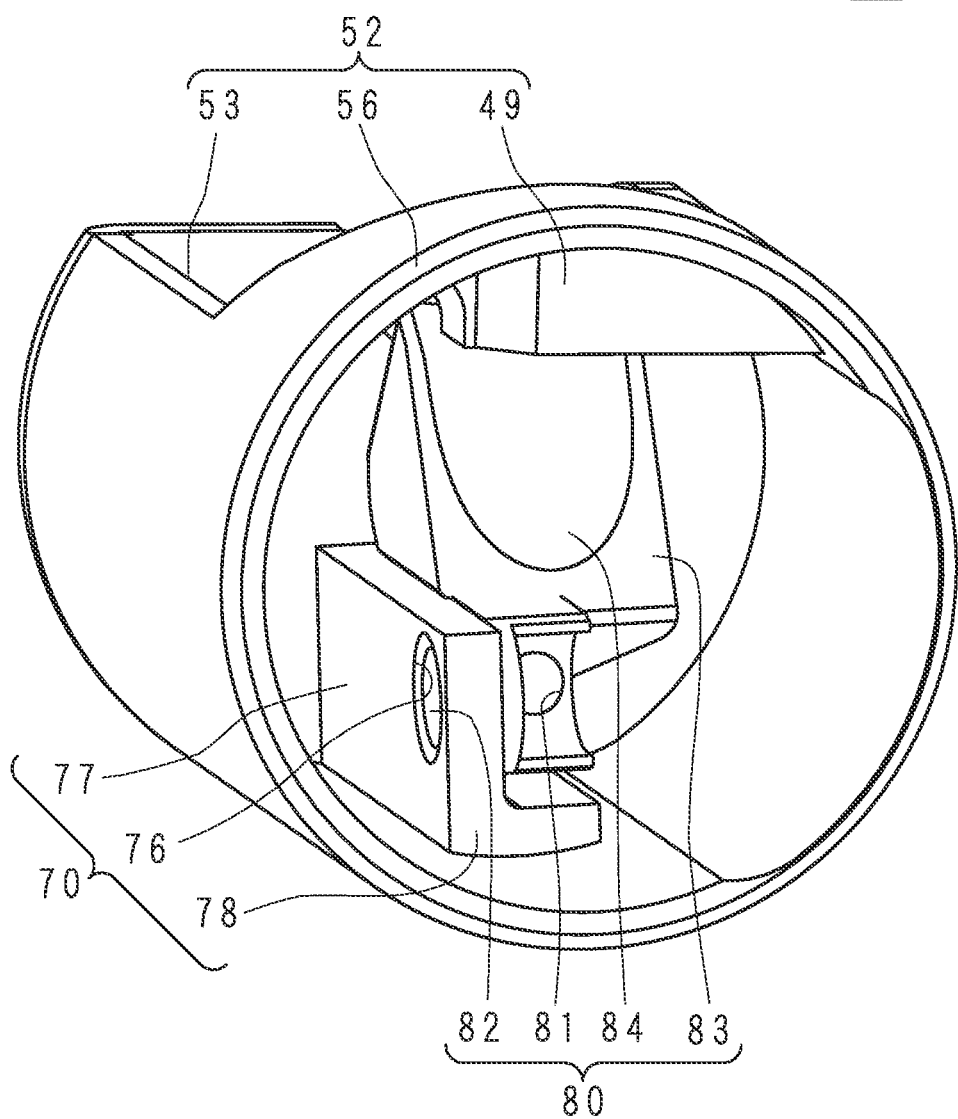
FIG. 4 is a perspective view of a cap.

FIG. 4 is a perspective view of a cap 50. FIG. 4 is a perspective view of a cap 50 when viewed from the attachment side to the endoscope 10. The cap 50 has a cover 52, a pedestal 70 and an elevator 80. The cover 52 has a bottomed cylindrical shape having an opening end 56 at one end thereof and a bottom at the other end thereof. The cover 52 has, at the opening end 56 side of the window part 53, a protrusion 49 which protrudes inward.

The pedestal 70 has a first wall 77 rising toward the window part 53 from the inner surface of the cover 52 that is opposed to the window part 53, and a second wall 78 extending from the first wall 77 on the cover 52 side along the inner surface of the cover 52. The first wall 77 has the shape of a plate with its wide surface being parallel to the axial direction of the cover 52.

The pedestal 70 has an elevator attachment hole 76 penetrating through the first wall 77. The pedestal 70 is fixed to the inner surface of the cover 52 by adhesion or welding while the elevator 80 is pivotally attached to the elevator attachment hole 76. The pivot here means rotary motion within a predetermined angle range.

Figure 5:
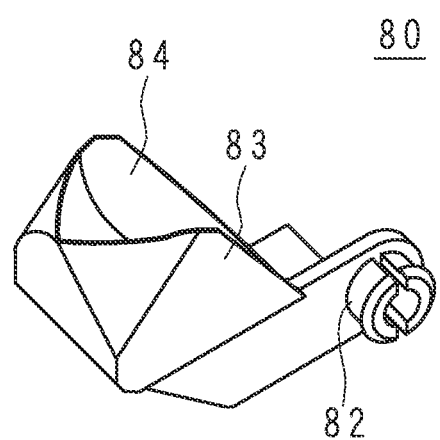
FIG. 5 is a perspective view of an elevator.

FIG. 5 is a perspective view of the elevator 80. The configuration of the elevator 80 will be described with reference to FIGS. 4 and 5. The elevator 80 has an elevator shaft 82, an elevating part 83 and a lever connection part 81.

The elevator shaft 82 is a columnar shaft with an expanding slot. The elevator shaft 82 has, at an end thereof, a retainer with a diameter one size larger than that of the elevator shaft 82. The elevating part 83 is disposed in a direction intersecting the central axis of the elevator shaft 82. The elevating part 83 has, at one surface thereof, a spoon-shaped recess 84 which is wider at a side distant from the elevator shaft 82.

The lever connection part 81 is located at the elevator shaft 82 side of the elevating part 83. The lever connection part 81 is a round hole opened at the inner surface of a cylindrical surface that is coaxial with the elevator shaft 82 so as to have an orientation intersecting the elevator shaft 82. More specifically, the central axis of the elevator shaft 82 is orthogonal to the central axis of the lever connection part 81. The lever connection part 81 may be a rectangular hole, an elliptical hole or the like. The lever connection part 81 may or may not penetrate through the elevating part 83. In the following description, the lever connection part 81 of a concave shape may also be referred to as a connection concave part.

The elevator shaft 82 is inserted into the elevator attachment hole 76. The elevator 80 may pivot around the elevator shaft 82 with respect to the pedestal 70. The retainer located at an end of the elevator shaft 82 prevents the once inserted elevator shaft 82 from coming off the elevator attachment hole 76. The recess 84 is opposed to the window part 53.

An assembly method for the cap 50 will be described with reference to FIGS. 4 and 5. First, the elevator 80 is attached to the pedestal 70 so as to be able to pivot. More specifically, the elevator shaft 82 is inserted into the elevator attachment hole 76.

Subsequently, the pedestal 70 is fixed to the inner surface of the cover 52. More specifically, the pedestal 70 in which adhesive is applied to one surface of the second wall 78 is inserted into the inner surface of the cover 52 through the opening end 56 side. The adhesive is cured while the surface of the second wall 78 applied with the adhesive is pressed against the inner surface of the cover 52. The direction of inserting the elevator shaft 82 into the elevator attachment hole 76 intersects with the direction of inserting the pedestal 70 into the cover 52.

Figure 6:
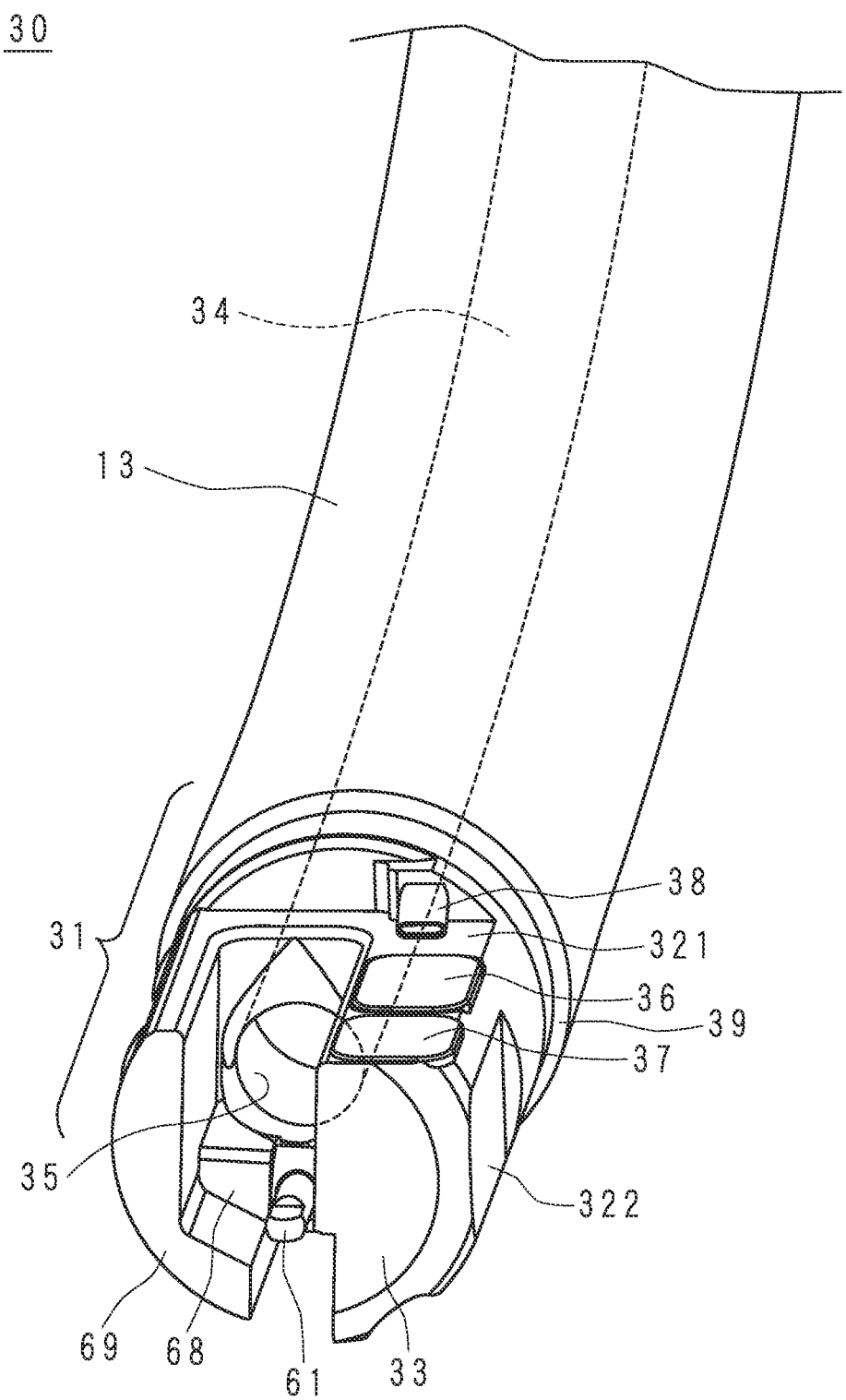
FIG. 6 is a perspective view of the distal end of the insertion part before the cap is attached.

FIG. 6 is a perspective view of the distal end of the insertion part 30 before the cap 50 is attached. The distal end portion 31 has a substantially columnar shape, and is divided into an optics housing 33 and a lever chamber 69 by a groove formed from the distal side to the proximal side at a position offset from the center. The channel outlet 35 is opened at the bottom of the groove. A bar-like elevator connection part 61 is exposed near the channel outlet 35. The elevator connection part 61 will be described later.

The distal end portion 31 has a first planar part 321 along the longitudinal direction of the insertion part 30. At the optics housing 33 side of the first planar part 321, the observation window 36 and the illumination window 37 are disposed. At the proximal side of the observation window 36, a nozzle 38 for injecting water and air to the observation window 36 to clean the observation window 36 is provided. At the outside of the optics housing 33, a second planar part 322 is provided.

The lever chamber 69 is hollow. The lever chamber 69 has a support wall 68 on the optics housing 33 side. The distal end portion 31 has a cap fixing groove 39 at the outer periphery thereof on the proximal side.

Figure 7:
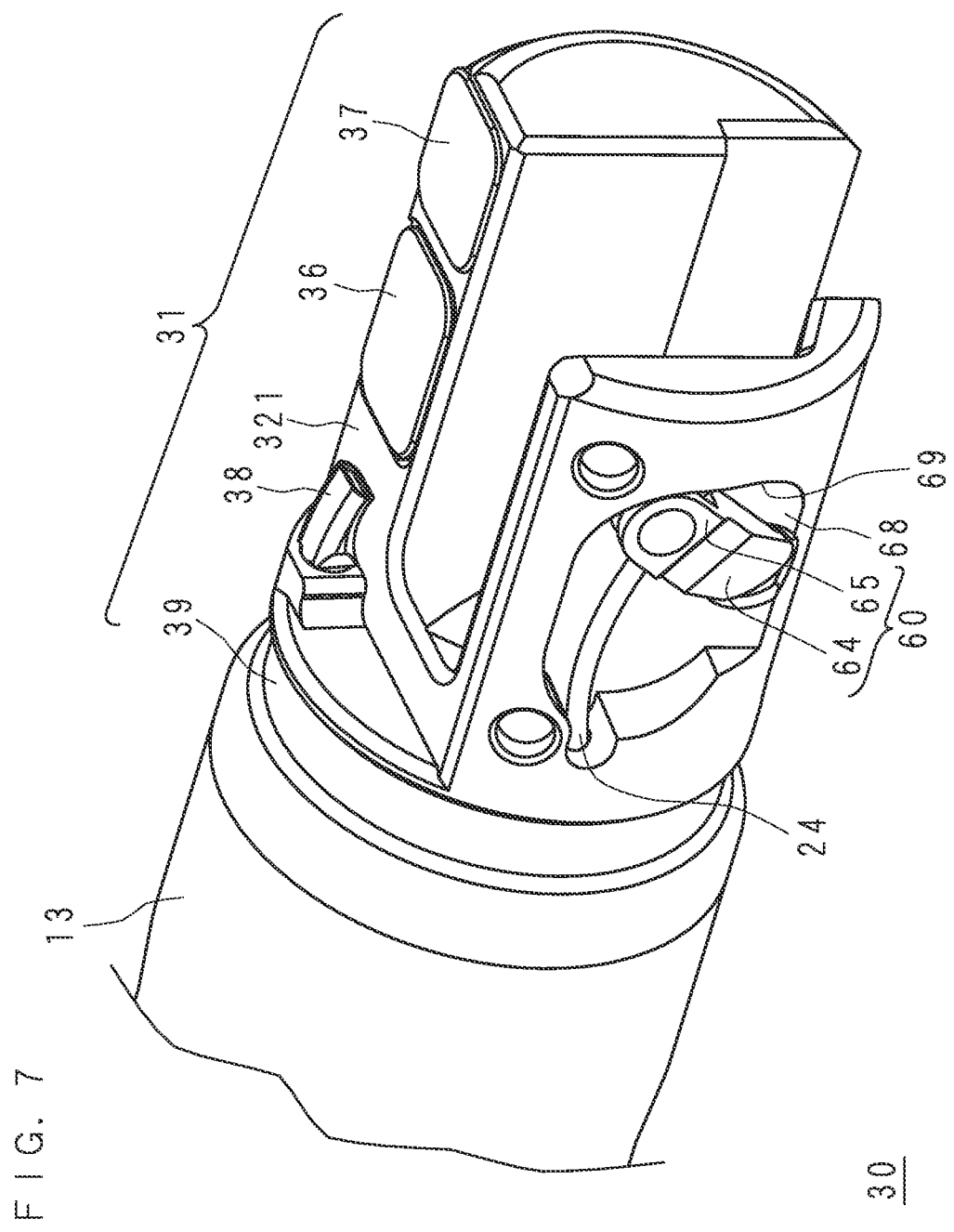
FIG. 7 is a perspective view of the distal end of the insertion part before the cap is attached.

FIG. 7 is a perspective view of the distal end of the insertion part 30 before the cap 50 is attached. FIG. 7 illustrates a state where a lever chamber lid 67 (see FIG. 11) is removed so as to show the inside of the lever chamber 69.

A pivot connection part 64 and a wire fixing part 65 are accommodated inside the lever chamber 69. The wire fixing part 65 is connected to an end of the elevating wire 24.

The elevating wire 24 passes through the insertion part 30 and is connected to the elevator operation lever 21 (see FIG. 1). More specifically, the elevating wire 24 is inserted into a guide tube (not illustrated) having an inner diameter somewhat larger than the outer diameter of the elevating wire 24. The guide tube (not illustrated) penetrates through the insertion part 30 along the longitudinal direction. Thus, the distal end of the elevating wire 24 moves back and forth in conjunction with the operation of the elevator operation lever 21. The elevating wire 24 is an example of the pivot part according to the present embodiment. The elevating wire 24 is operated remotely by the elevator operation lever 21.

Figure 8:
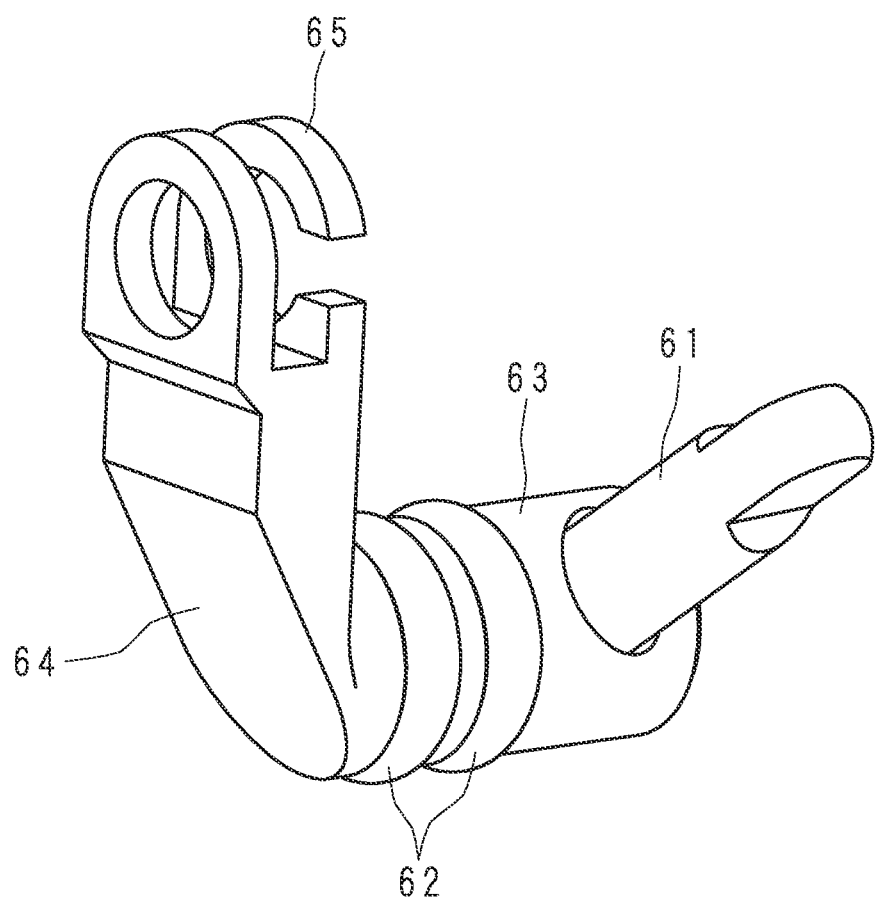
FIG. 8 is a perspective view of a lever.

FIG. 8 is a perspective view of a lever 60. The lever 60 has a lever shaft 63, an elevator connection part 61, a pivot connection part 64, a wire fixing part 65 and two O-rings 62.

The lever shaft 63 is a columnar shaft. The columnar elevator connection part 61 protrudes from the side surface of the lever shaft 63 in a direction intersecting the central axis of the lever shaft 63. From an end of the lever shaft 63, the pivot connection part 64 protrudes in a direction intersecting the central axis of the lever shaft 63, which is different from the protruding direction of the elevator connection part 61. A wire fixing part 65 having an expanding slot is provided at an end of the pivot connection part 64. Two O-rings 62 are fixed at a portion of the lever shaft 63 that is located between the elevator connection part 61 and the pivot connection part 64.

Figure 9:
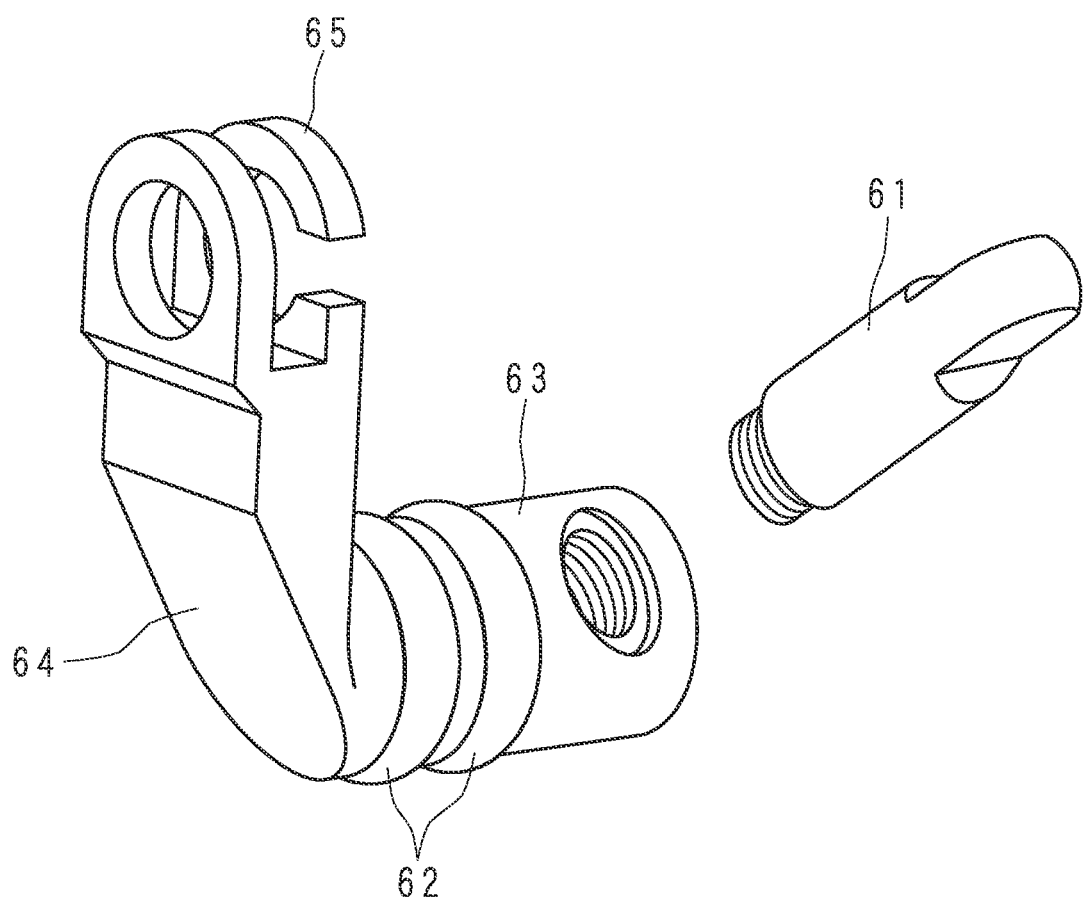
FIG. 9 is an exploded perspective view of the lever.

FIG. 9 is an exploded perspective view of the lever 60. The elevator connection part 61 has a male thread at one end thereof. The lever shaft 63 has a female thread at a side surface thereof. After the lever shaft 63 that received the O-rings 62 is inserted into the hole opened at the support wall 68, the male thread of the elevator connection part 61 is coupled with the female thread of the lever shaft 63, so that the lever 60 is pivotally supported by the support wall 68. By holding and rotating the planar part located at the end of the elevator connection part 61 with a tool such as needle-nose pliers, the elevator connection part 61 and the lever shaft 63 may securely be coupled with each other.

Figure 10:
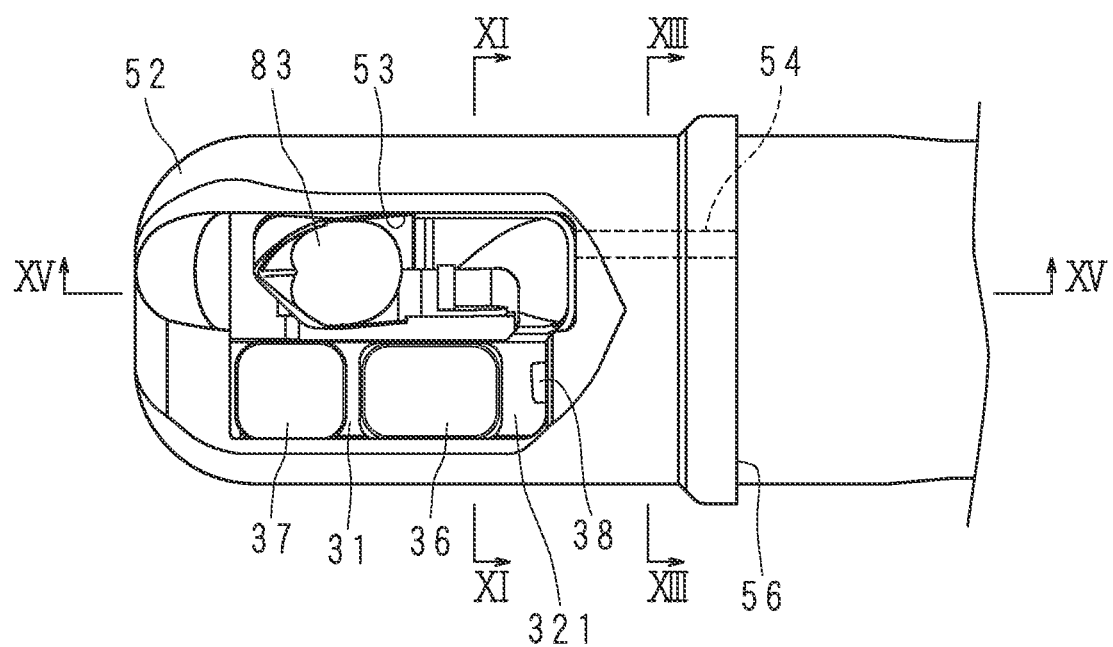
FIG. 10 is a side view of the distal end of the insertion part.

FIG. 10 is a side view of the distal end of the insertion part 30. FIG. 10 illustrates the distal end of the insertion part 30 to which the cap 50 is attached when viewed from the window part 53 side. The cap 50 is fixed to the insertion part 30 by being pressed from the distal side of the distal end portion 31. The end face of the lever chamber 69 on the distal side abuts the bottom of the cap 50. The observation window 36, the illumination window 37 and the elevating part 83 are seen inside the window part 53.

Figure 11:
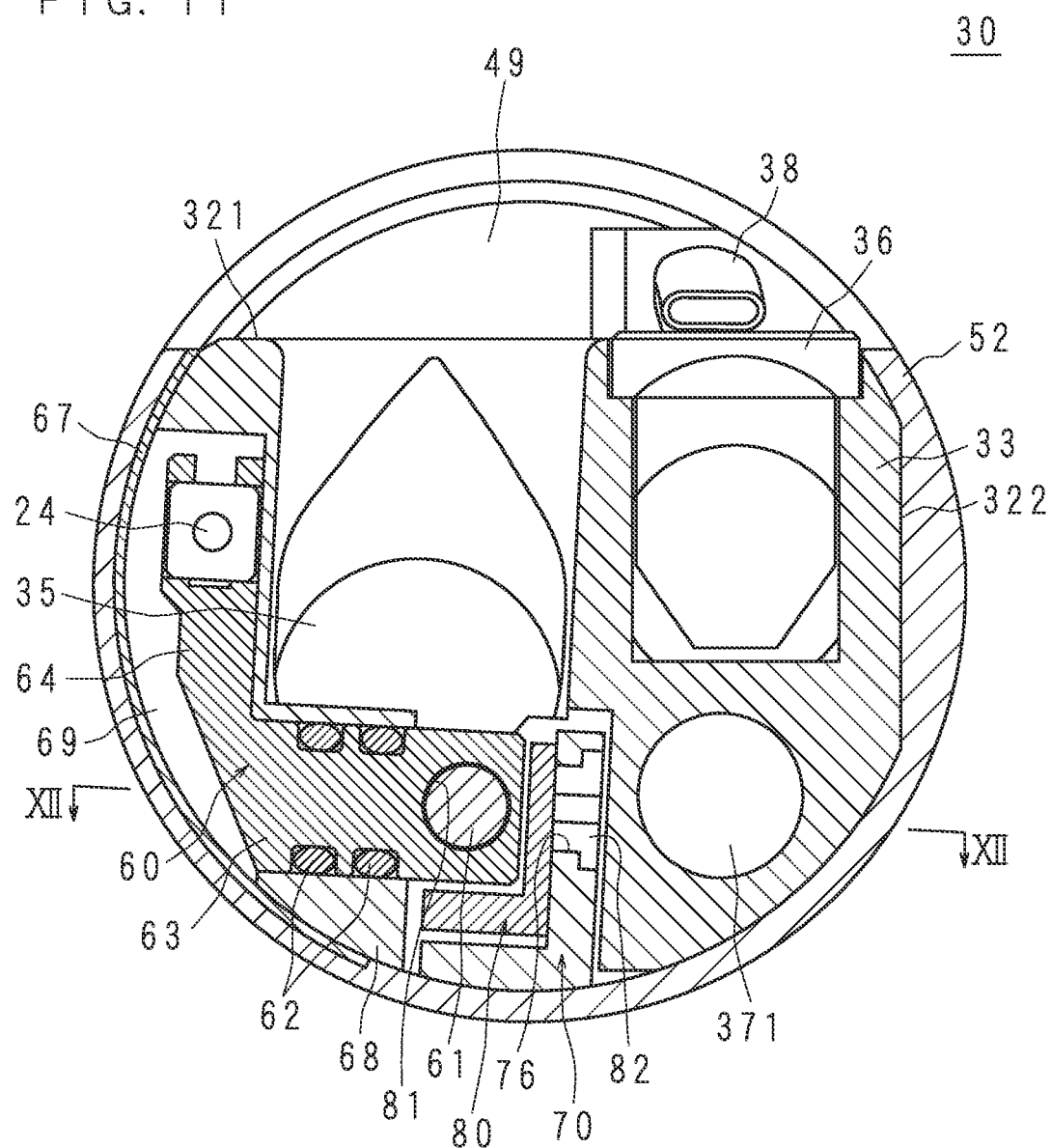
FIG. 11 is a section view of the insertion part taken along the line XI-XI in FIG. 10.

FIG. 11 is a section view of the insertion part 30 taken along the line XI-XI in FIG. 10. The lever chamber 69 is sealed with the lever chamber lid 67. A hole through which the lever shaft 63 penetrates the support wall 68 is sealed with the two O-rings 62. The structure described above prevents water or the like from intruding into the lever chamber 69.

An observation optical system such as lens is disposed under the observation window 36 in FIG. 11. A video image photographed by an image sensor (not illustrated) via the observation optical system is processed by a video processor (not illustrated) and is displayed on a display device.

A light guide fiber 371 is disposed under the observation optical system in FIG. 11. The light guide fiber 371 is connected to the illumination window 37. The light guide fiber 371 guides illumination light from a light source device (not illustrated) to the illumination window 37.

The cover 52 has a planar part corresponding to the second planar part 322 at the inner surface thereof. The second planar part 322 abuts the planar part of the cover 52 so as to prevent the cap 50 from rotating.

Figure 12:
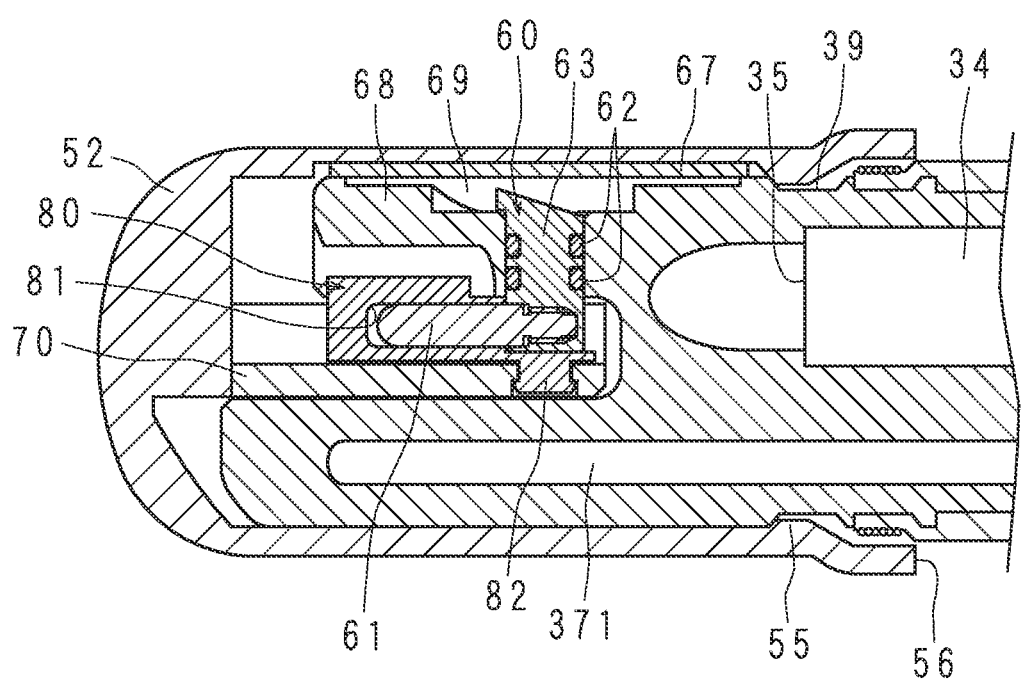
FIG. 12 is a section view of the insertion part taken along the line XII-XII in FIG. 11.

FIG. 12 is a section view of the insertion part 30 taken along the line XII-XII in FIG. 11. The XII-XII section is a cross section passing the central axis of the lever shaft 63 and the central axis of the elevator shaft 82 along the longitudinal direction of the insertion part 30. As illustrated in FIGS. 11 and 12, the central axis of the lever shaft 63 and the central axis of the elevator shaft 82 are coaxially arranged. The lever 60 is provided at the distal end of the insertion part 30 of the endoscope 10 so as to be able to pivot around the lever shaft 63.

The elevator connection part 61 is inserted into the lever connection part 81. The elevator connection part 61 and the lever connection part 81 connect the lever 60 and the elevator 80 with each other. That is, in the case where the lever 60 pivots around the lever shaft 63, the elevator 80 also pivots integrally with the lever 60. Since the central axis of the lever shaft 63 and the central axis of the elevator shaft 82 are coaxially arranged, the elevator 80 smoothly operates together with the lever.

As illustrated above, when the cap 50 is mounted to the distal end portion 31 of the endoscope 10, the elevator 80 is connected to the lever 60. Connection here means the state where the elevator 80 and the lever 60 are connected while pivoting together if the lever 60 pivots.

In the following description, the elevator connection part 61 having the shape of a projection as illustrated in FIG. 12 may also be referred to as an elevator projection. The elevator projection has a shape which may be inserted into the connection concave part illustrated with reference to FIG. 5.

The cover 52 has, at the inner surface thereof, an attachment projection 55 extending in a line along the edge of the opening end 56. The attachment projection 55 is inclined more gently on the opening end 56 side compared to the bottom side of the cover 52. The attachment projection 55 is engaged with the cap fixing groove 39 formed at an outer periphery of the distal end portion 31.

Because of the gentle inclination on the opening end 56 side, fitting of the attachment projection 55 into the cap fixing groove 39 is relatively easy when the cap 50 is pressed onto the distal end of the insertion part 30. Since the inclination on the bottom side is steep, on the other hand, the cap 50 that had been once fixed is unlikely to come off the insertion part 30. After the cap 50 is pressed onto the distal end of the insertion part 30, a medical tape or the like may be wound around the opening end 56 of the cap 50 as well as the insertion part 30. This can further secure the fixed cap 50.

Figure 13:
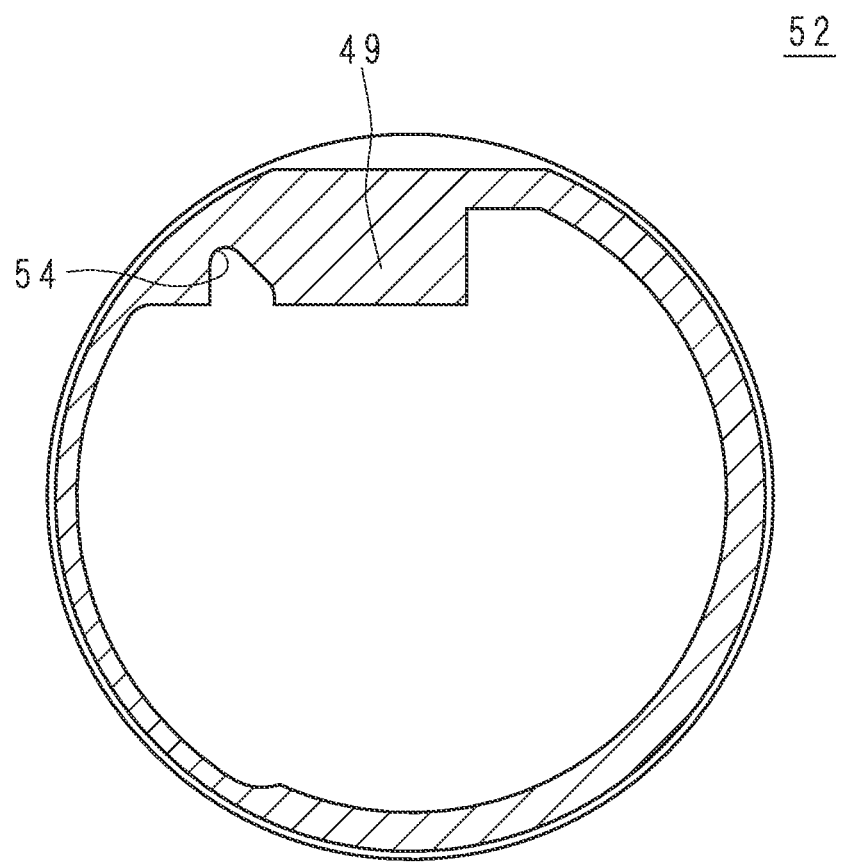
FIG. 13 is a section view of the cover taken along the line XIII-XIII in FIG. 10.

FIG. 13 is a section view of the cover 52 taken along the line XIII-XIII in FIG. 10. In FIG. 13, members other than the cover 52 are not illustrated. The surface of the protrusion 49 that faces the center of the cover 52 is a flat surface. The first planar part 321 abuts the protrusion 49 so as to prevent the cap 50 from rotating.

The cover 52 has a cutout 54 having a substantially triangular cross section at the inner surface thereof. As indicated by the broken lines in FIG. 10, the cutout 54 is a groove formed between the edge of the window part 53 and the opening end 56.

Figure 14:
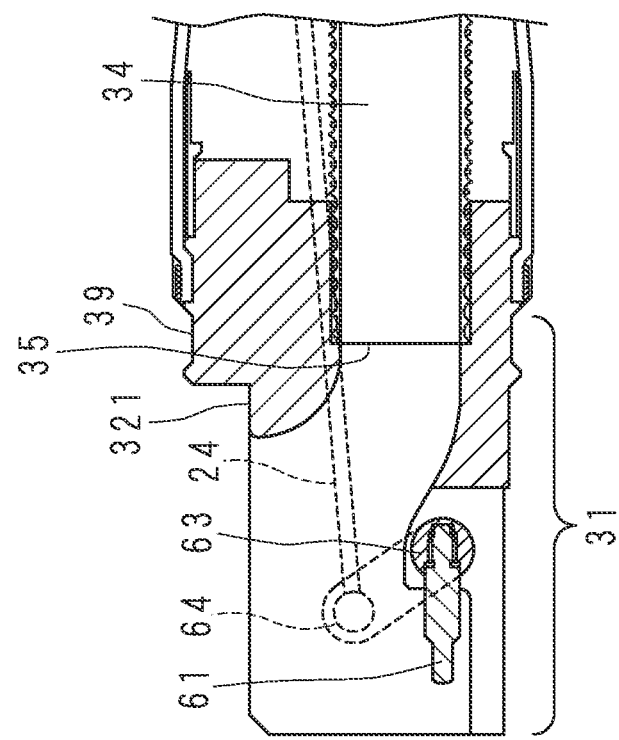
FIG. 14 is a section view illustrating the procedure of attaching the cap to the distal end of the insertion part.
Figure 14:
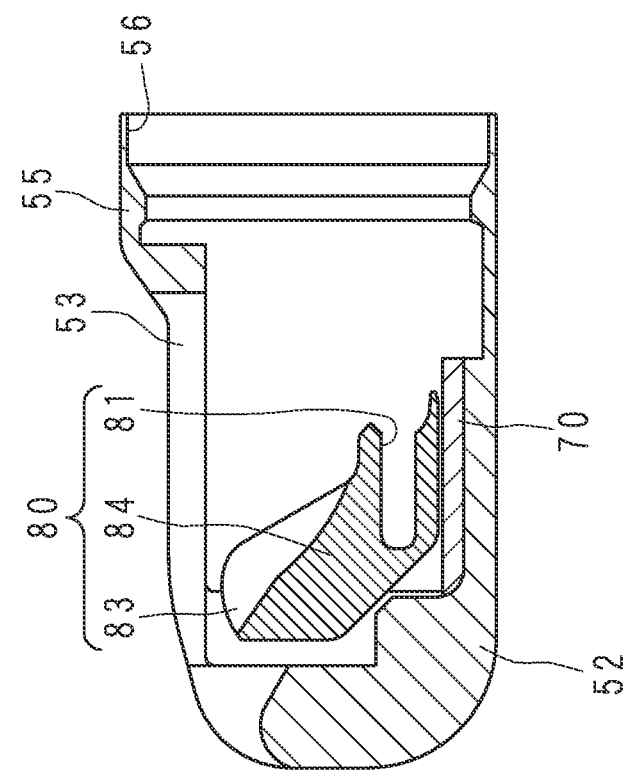

FIG. 14 is a section view illustrating the procedure of attaching the cap 50 to the distal end of the insertion part 30.

The elevator operation lever 21 is operated to direct the elevator connection part 61 toward the distal end of the insertion part 30. The elevator 80 in the cap 50 directs the lever connection part 81 toward the opening end 56.

In this state, the cap 50 is pressed onto the distal end portion 31 from the distal side. The cover 52 temporarily expands so that the attachment projection 55 is engaged into the cap fixing groove 39. This fixes the cap 50 to the distal end portion 31. As the elevator connection part 61 fits into the lever connection part 81, the lever 60 and the elevator 80 may pivot in an integrated manner. As described earlier, the end face of the lever chamber 69 on the distal side abuts the bottom of the cover 52, the first planar part 321 abuts the protrusion 49, and the second planar part 322 abuts the flat surface at the inner surface of the cover 52. This structure prevents the cap 50 from rotating and rattling.

Figure 15:
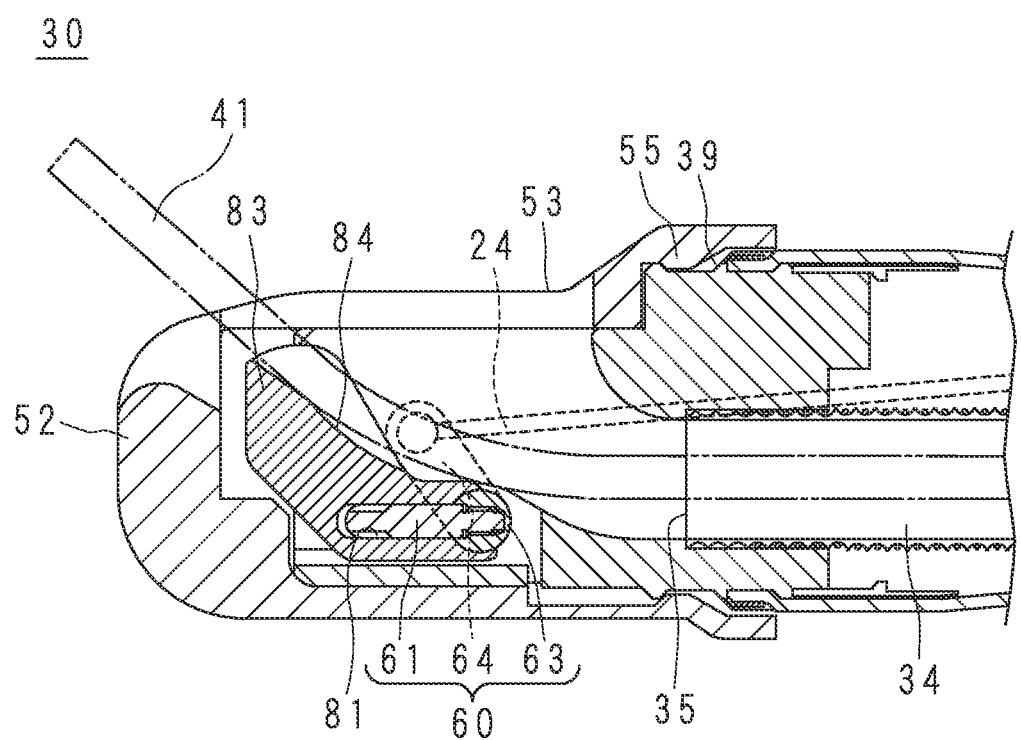
FIG. 15 is a section view of the insertion part taken along the line XV-XV in FIG. 10.
Figure 16:
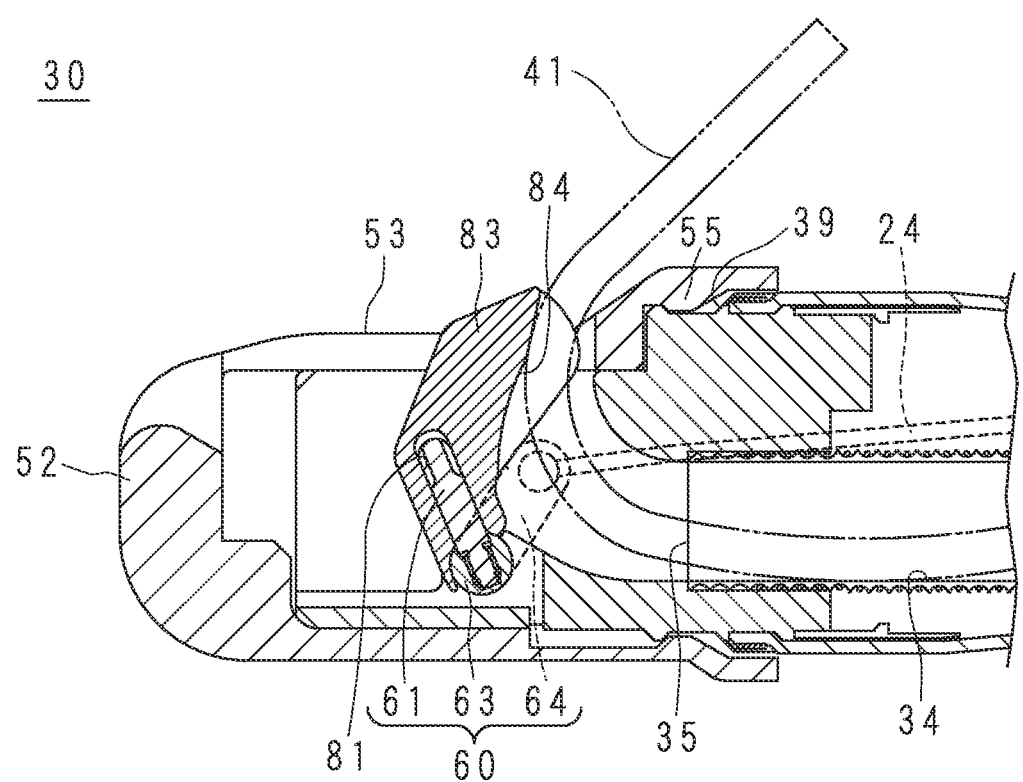
FIG. 16 is a section view of the endoscope in which an elevator is elevated.

FIG. 15 is a section view of the insertion part 30 taken along the line XV-XV in FIG. 10. FIG. 16 is a section view of the endoscope 10 in which the elevator 80 is elevated. The movement of the elevator 80 will be described with reference to FIGS. 15 and 16.

In the state illustrated in FIG. 15, the elevator 80 is accommodated inside the cover 52. The recess 84 is located at a position that allows the treatment tool tip end 41 protruding from the channel outlet 35 to bend gently upward in FIG. 15.

As the elevator operation lever 21 moves, the elevating wire 24 connected to the elevator operation lever 21 is pulled toward the proximal side. Being pulled by the elevating wire 24, the lever 60 pivots around the lever shaft 63. Since the elevator connection part 61 is connected to the lever connection part 81, the elevator 80 also pivots to rise together with the lever 60. As a result, the distance between the elevator 80 and the window part 53 changes.

FIG. 16 illustrates the state where the elevator 80 pivots. Being pushed by the elevator 80, the treatment tool tip end 41 protruding from the channel outlet 35 is bent toward the proximal side. The pivoting movement for the elevator 80 to rise as illustrated in FIG. 16 may also be referred to as "the elevator 80 is elevated" in the description below. The bending of the treatment tool tip end 41 by being pushed by the elevated elevator 80 may also be referred to as "the treatment tool 40 is elevated" in the description below. The operation of the elevator operation lever 21 may adjust the degree of elevation of the treatment tool 40.

A method of using the endoscope 10 according to the present embodiment will now be summarized. The endoscope 10 is stored in a state where the cap 50 is removed and is subjected to cleaning or the like. The cap 50 is provided in a sterilized package. The user takes out the cap 50 from the sterilized package and attaches the cap 50 to the distal end portion 31 of the endoscope 10.

The user inserts the insertion part 30 through the mouth of a subject to be examined. While viewing a video image photographed via the observation window 36, the user guides the distal end of the insertion part 30 to a target site. The user inserts the treatment tool 40 or the like according to a purpose through the channel inlet 22. After confirming that the treatment tool tip end 41 protrudes from the distal end of the insertion part 30 and is located near the target site, the user operates the elevator operation lever 21 to guide the treatment tool tip end 41 to the target site. The user performs a necessary treatment or the like and then pulls out the treatment tool 40 from the channel 34. The user pulls out the endoscope 10 from the subject, and terminates the examination or treatment.

The cover 52 may easily be detached by breaking it through the cutout 54. The cap 50 according to the present embodiment is so-called single use, and is discarded after one use.

The user performs a process such as cleaning on the endoscope 10 after the cap 50 is removed, to prepare for the next use. As illustrated in FIG. 6, the endoscope 10 after the cap 50 is detached has no elevator 80. The elevator connection part 61 used when the elevator 80 is fixed is exposed at the distal end portion 31, as illustrated in FIG. 6. Since the lever chamber 69 is sealed with the lever chamber lid 67 and the O-rings 62, no body fluid or the like is adhered to the path of the elevating wire 24.

It is therefore possible to provide the endoscope 10 that has short process time between cases and that may efficiently be put into practice, since no special cleaning work or the like is necessary for cleaning the complicated structure around the elevator 80 and the elevating wire 24.

The endoscope 10 according to the present embodiment is provided with the elevator 80 and is of the side view type, which makes it suitable for diagnosis and treatment of duodenum and pancreaticobiliary duct areas. In particular, for the case of performing procedures such as endoscopic retrograde cholangio pancreatography (ERCP), endoscopic sphincterotomy (EST), endoscopic biliary drainage (EBD) and so forth, the endoscope 10 according the present embodiment is suitable. This is because, in these procedures, treatment or the like is performed by guiding the treatment tool 40 into the duodenum papilla on the duodenal wall as well as the pancreas duct, common bile duct and the like that are opened at the duodenum papilla.

According to the present embodiment, it is possible to provide the cap 50 that may prevent it from being reused by mistake, since the cap 50 is detached from the insertion part 30 by breaking the cover 52 after use. According to the present embodiment, it is possible to provide the endoscope 10 to/from which the elevator 80 and the cap 50 may be attached and detached. According to the present embodiment, it is also possible to provide the endoscope 10 including the elevator 80, which may be subjected to a process such as cleaning with procedures similar to those for a regular endoscope without the elevator 80.

The endoscope 10 of the side view type may also be referred to as a side view endoscope. Likewise, the endoscope 10 suitable for diagnosis or the like of the duodenum and pancreaticobiliary duct areas may also be referred to as a duodenoscope.

According to the present embodiment, since the pedestal 70 and the cover 52 are separate members, their respective shapes are simple. It is thus possible to manufacture them at lower cost by, for example, injection molding.

For the pivot part, an expandable shape memory alloy (SMA) actuator may also be employed instead of the elevating wire 24. In such a case, one end of the SMA actuator is fixed to the wire fixing part 65 whereas the other end thereof is fixed to the distal end portion 31. A heater is placed around the SMA actuator. The heater is configured to operate in conjunction with the movement of the elevator operation lever 21.

As the heater operates and the SMA actuator contracts, the lever 60 and the elevator 80 pivot. For the pivot part, any other linear actuator may also be employed.

A pivoting actuator such as a small motor may also be employed for the pivot part. The small motor is disposed in the lever chamber 69, and the motor shaft and the lever shaft 63 may be connected with each other to allow the lever 60 to pivot.

In the case where an actuator is employed for the pivot part, the elevator 80 may be operated by a means not using a hand of the user, such as voice control, for example.

The cap 50 may also be provided in the state where the elevator 80 and the cover 52 or the pedestal 70 are temporarily fixed to each other by an adhesive material or the like while the lever connection part 81 faces the opening end 56. Accordingly, the cap 50 which is used in a simple manner may be provided while eliminating the trouble of confirming the orientation of the elevator 80 before the cap 50 is attached to the insertion part 30.

It is also possible for the user to select and use a cap 50 with a specification according to a procedure from multiple types of caps 50 with different specifications. For example, a cap 50 provided with a stopper that restricts the pivotal range of the elevator 80 to be narrow may also be provided. In the case of using a combination of expensive and precise instruments such as an ultrasound probe or ultra-slim endoscope, for example, the narrowing of the pivotal range may prevent such instruments from being damaged by excessive bending.

In the case where the recess 84 has a shape contoured to the profile of the treatment tool tip end 41, the treatment tool 41 is unlikely to sway to the left and right at elevation, and thus tends to be easily operated. Multiple types of caps 50 having elevators 80 with recesses 84 of different shapes may be provided. For example, a cap 50 with a recess 84 having a shape that can easily hold a thin treatment tool 40 may be used to facilitate precise operation of the thin treatment tool 40 such as a guide wire.

Accordingly, the endoscope 10 for which the user may select and use the cap 50 suitable for a purpose may be provided.

The endoscope 10 may be a so-called ultrasound endoscope provided with an ultrasound transducer at the distal end. Here, the cap 50 may preferably have a hole at the bottom through which the ultrasound transducer is inserted. The endoscope 10 may also be an endoscope directed to a lower gastrointestinal tract. The endoscope 10 may also be a so-called rigid endoscope provided with a rigid insertion part 30. The endoscope 10 may also be a so-called industrial endoscope used for inspection of engine, pipework and so forth.

The lever connection part 81 may have the shape of a projection whereas the elevator connection part 61 may be a concave part corresponding to the lever connection part 81.

The cover 52 may not necessarily have the cutout 54. In such a case, the user may pull and deform the cover 52 to remove the cap 50 from the insertion part 30. The user may also use a tool such as a scalpel to remove the cap 50 from the insertion part 30.

The cap 50 may be reusable. In such a case, the user visually checks the cap 50 removed from the insertion part 30 and, if it is not broken, reuses the cap 50 after performing a process such as cleaning. Since the opening end 56 of the cap 50 is wide open, a process such as cleaning may more easily be performed compared to the state where the cap 50 stays attached to the insertion part 30.

Because of its small size, the cap 50 may easily be put into a sterilized package for autoclave sterilization, for example.

The lever connection part 81 may have the shape of a projection whereas the elevator connection part 61 may be a concave part corresponding to the lever connection part 81.

Embodiment 2

The present embodiment relates to a cap 50 which is easily assembled. Portions common to those in Embodiment 1 will not be described here.

Figure 17:
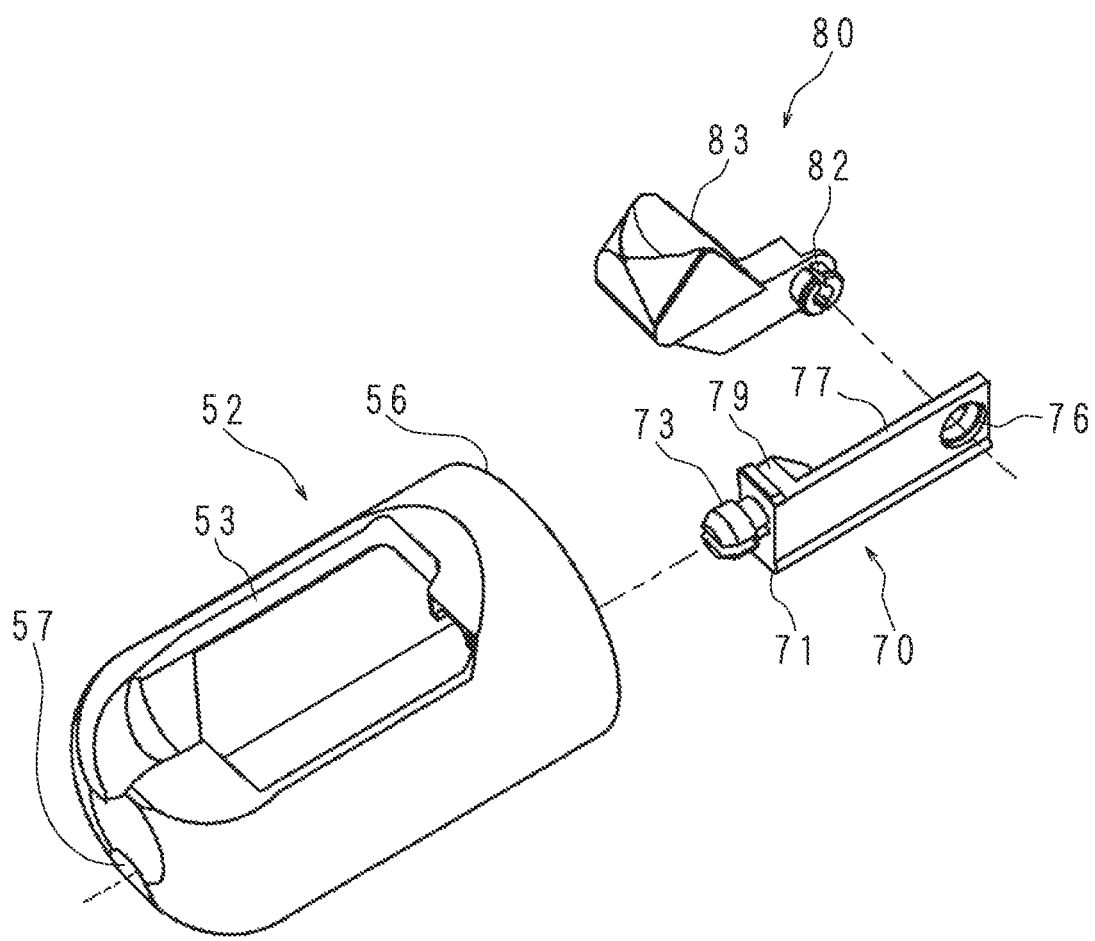
FIG. 17 is an exploded perspective view of a cap according to Embodiment 2.
Figure 18:
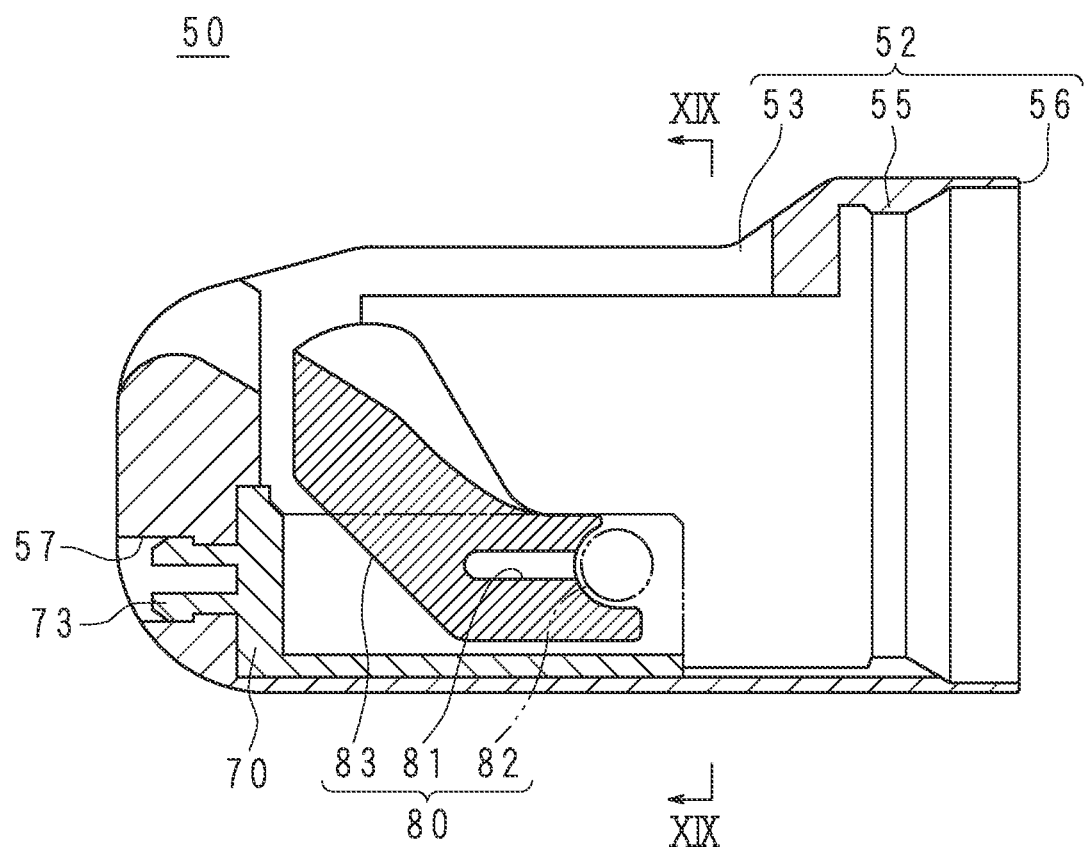
FIG. 18 is a section view of the cap according to Embodiment 2.
Figure 19:
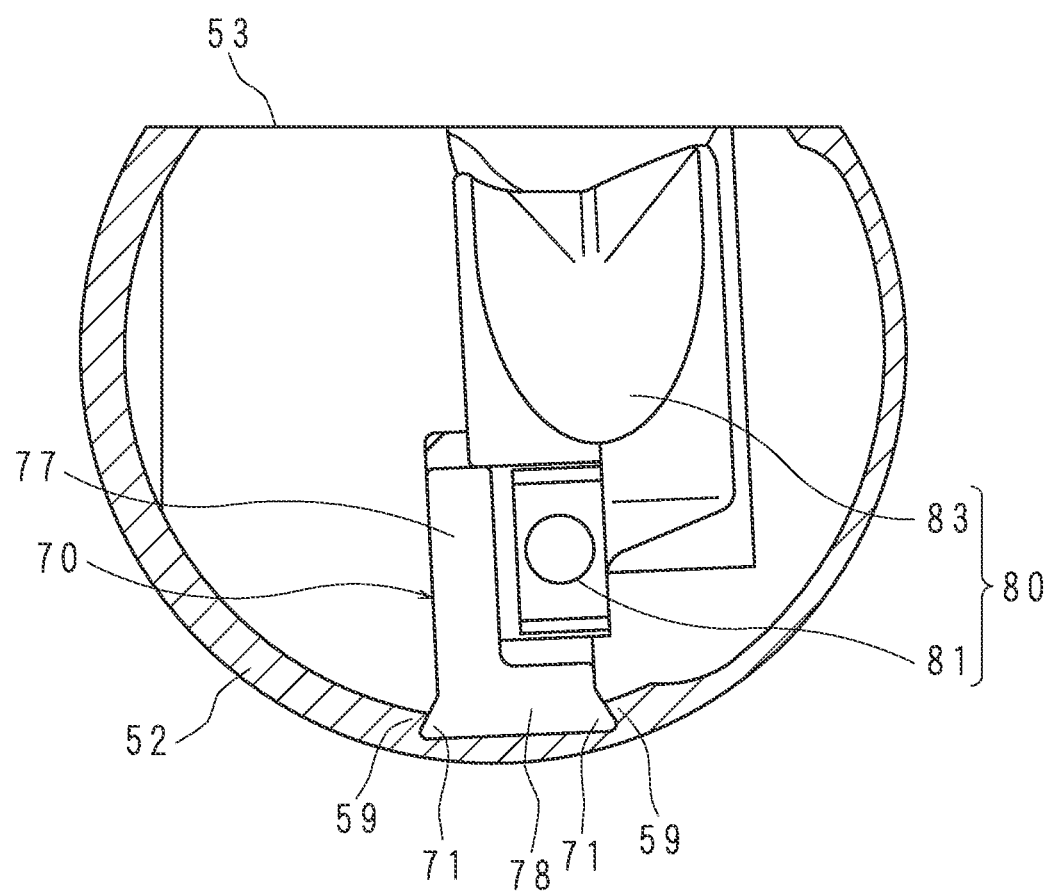
FIG. 19 is a section view of the cap according to Embodiment 2 taken along the line XIX-XIX in FIG. 18.

FIG. 17 is an exploded perspective view of a cap 50 according to Embodiment 2. FIG. 18 is a section view of the cap 50 according to Embodiment 2. FIG. 19 is a section view of the cap 50 according to Embodiment 2 taken along the line XIX-XIX in FIG. 18. The configuration of the cap 50 according to the present embodiment will be described with reference to FIGS. 17 to 19.

The cap 50 has a cover 52, a pedestal 70 and an elevator 80. The pedestal 70 has a first wall 77, a second wall 78 and a third wall 79. The first wall 77 is a substantially rectangular plate. The second wall 78 is a substantially rectangular plate which extends substantially perpendicular to the first wall 77 from the edge of a long side of the first wall 77. The third wall 79 is a substantially rectangular plate which extends in the same direction as the second wall 78 from the edge of a short side of the first wall 77.

At the first wall 77, an elevator attachment hole 76 is formed at an end distant from the third wall 79. The elevator attachment hole 76 is a round hole penetrating through the first wall 77. The third wall 79 is provided with a third fixing projection 73 on a surface opposite from the first wall 77. The third fixing projection 73 is a projection having an expanding slot. The third fixing projection 73 has, at an end thereof, a retainer with a diameter one size larger than that of the projection 73.

The second wall 78 has two pedestal edge projections 71 at the edges thereof on the long side of the surface opposite to the first wall. The pedestal edge projections 71 are projections protruding along the ridge line of the second wall 78.

The cover 52 has a pedestal fixing hole 57 at the bottom. The pedestal fixing hole 57 is a stepped round hole having an inner diameter on the outer surface side of the cover 52 larger than the outer diameter thereof on the inner surface side of the cover 52. The cover 52 has two first fixing projections 59 on the inner surface thereof. The first fixing projections 59 are two parallel projections protruding in directions facing each other. The distance between the two first fixing projections 59 corresponds to the distance between the two pedestal edge projections 71.

A method of assembling the cap 50 will now be described. First, the elevator 80 is pivotally attached to the pedestal 70. More specifically, the elevator shaft 82 is inserted into the elevator attachment hole 76. Subsequently, the pedestal 70 is fixed to the inner surface of the cover 52. More specifically, the pedestal 70 is inserted into the cover 52 while sliding between the two first fixing projections 59 from the opening end 56 side. As illustrated in FIG. 17, the direction of inserting the elevator shaft 82 into the elevator attachment hole 76 intersects with the direction of inserting the pedestal 70 into the cover 52.

As illustrated in FIG. 19, the pedestal edge projections 71 and the first fixing projections 59 are engaged with each other to fix the pedestal 70 to the inner surface of the cover 52. That is, the two first fixing projections 59 form so-called dovetail grooves, and the pedestal 70 serves as a so-called dovetail tenon to be fit into the dovetail grooves.

The pedestal 70 is pressed against the bottom of the cover 52. The third fixing projection 73 is inserted into the pedestal fixing hole 57. The thick diameter part at the tip end of the third fixing projection 73 is engaged with the stepped part of the pedestal fixing hole 57, to prevent the once-inserted third fixing projection 73 from coming off the pedestal fixing hole 57. The procedures described above complete the cap 50.

According to the present embodiment, the cap 50 which can easily be assembled by fitting three components of the cover 52, pedestal 70 and elevator 80 in order may be provided.

The cap 50 according to the present embodiment may also be reusable. In the case of reusing, the user preferably removes the pedestal 70 and the elevator 80 from the cover 52 after use, performs cleaning or the like, and thereafter assembles them for reuse.

More specifically, a jig or the like is used to pinch the third fixing projection 73 in directions of closing the expanding slot while pushing it toward the inner side of the cover 52, to remove the pedestal 70 from the cover 52. Furthermore, a jig or the like is used to pinch the elevator shaft 82 in directions of closing the expanding slot while pushing it, to remove the elevator 80 from the pedestal 70.

By disassembling the cap 50 into three components according to the procedures described above, a process such as cleaning may easily be performed. Before reusing, the cap 50 is assembled according to the procedures described earlier. This can provide the cap 50 that can easily be cleaned around the elevator 80 to be reused.

It is also possible to reuse the pedestal 70 and the elevator 80 while only the cover 52 employs a single use component. In such a case, the cutout 54 which helps to easily break the cover 52 may preferably be formed. Accordingly, the cap 50 which is easily removable after use and has reusable pedestal 70 and elevator 80 may be provided.

Upon inserting the pedestal 70 into the cover 52, an adhesive may be applied between the two first fixing projections 59 or the two pedestal edge projections 71. This allows the pedestal 70 and the cover 52 to be securely fixed to each other.

In the case of using an adhesive, only one of the first fixing projections 59 and one of the pedestal edge projections 71 may be employed. Here, the first fixing projection 59 and the pedestal edge projection 71 serve as abutting parts for positioning between the pedestal 70 and the cover 52.

Embodiment 3

The present embodiment relates to a cap 50 in which an elevator attachment hole 76 is formed by two components. Portions common to those in Embodiment 2 will not be described here.

Figure 20:
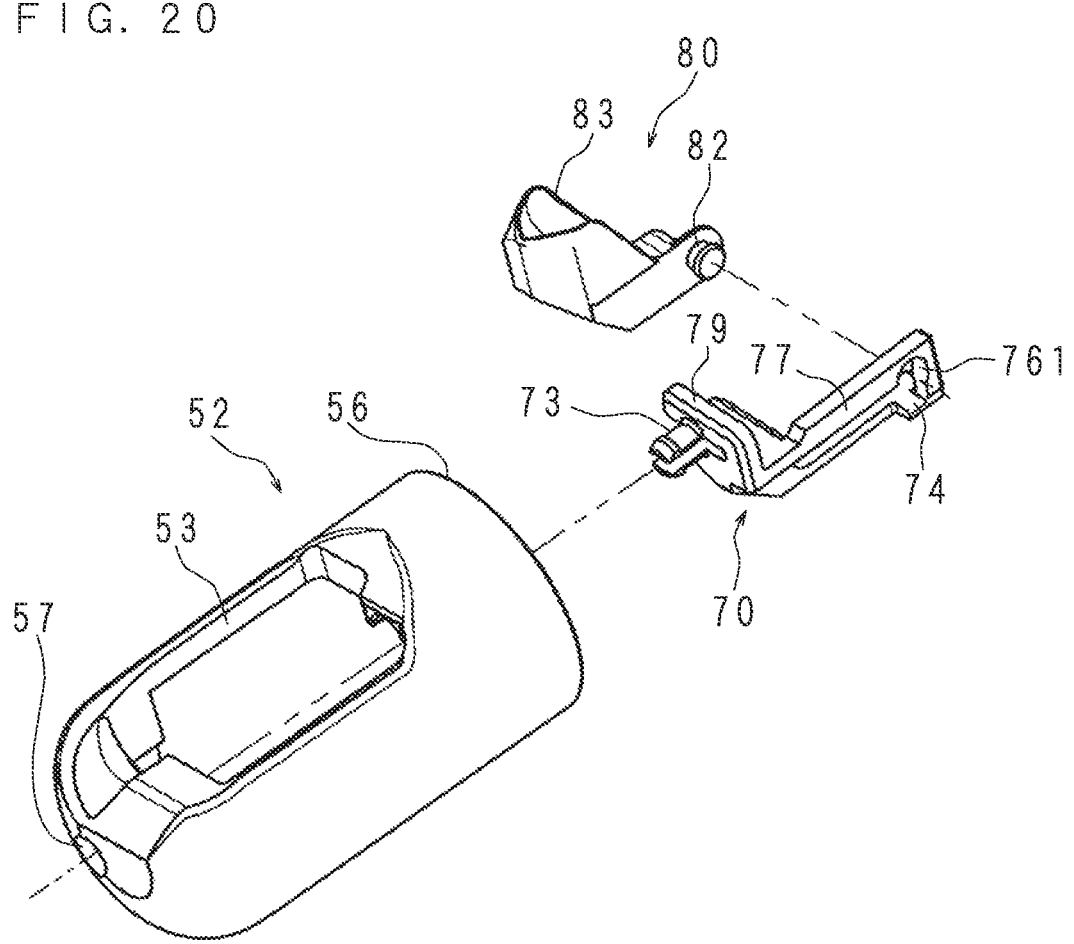
FIG. 20 is an exploded perspective view of a cap according to Embodiment 3.
Figure 21:
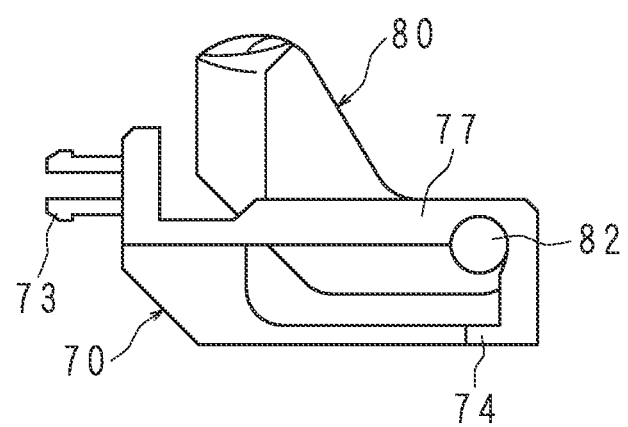
FIG. 21 is a side view of a pedestal and an elevator according to Embodiment 3 combined together.
Figure 22:
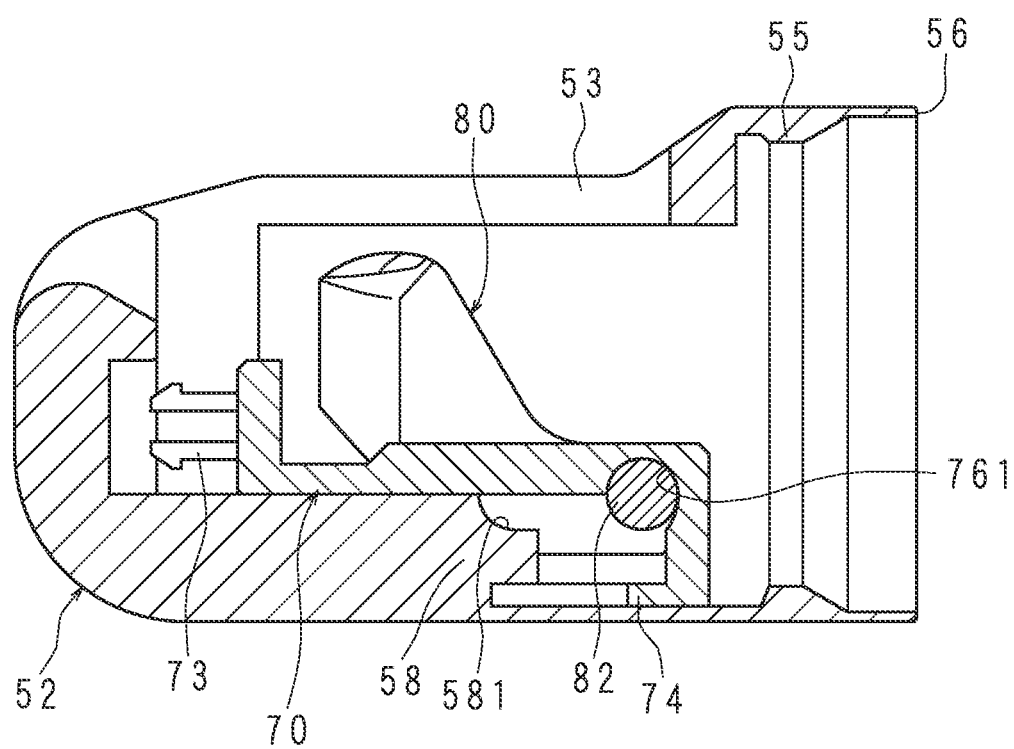
FIG. 22 illustrates the state where the cover and the pedestal according to Embodiment 3 are in the process of being combined together.
Figure 23:
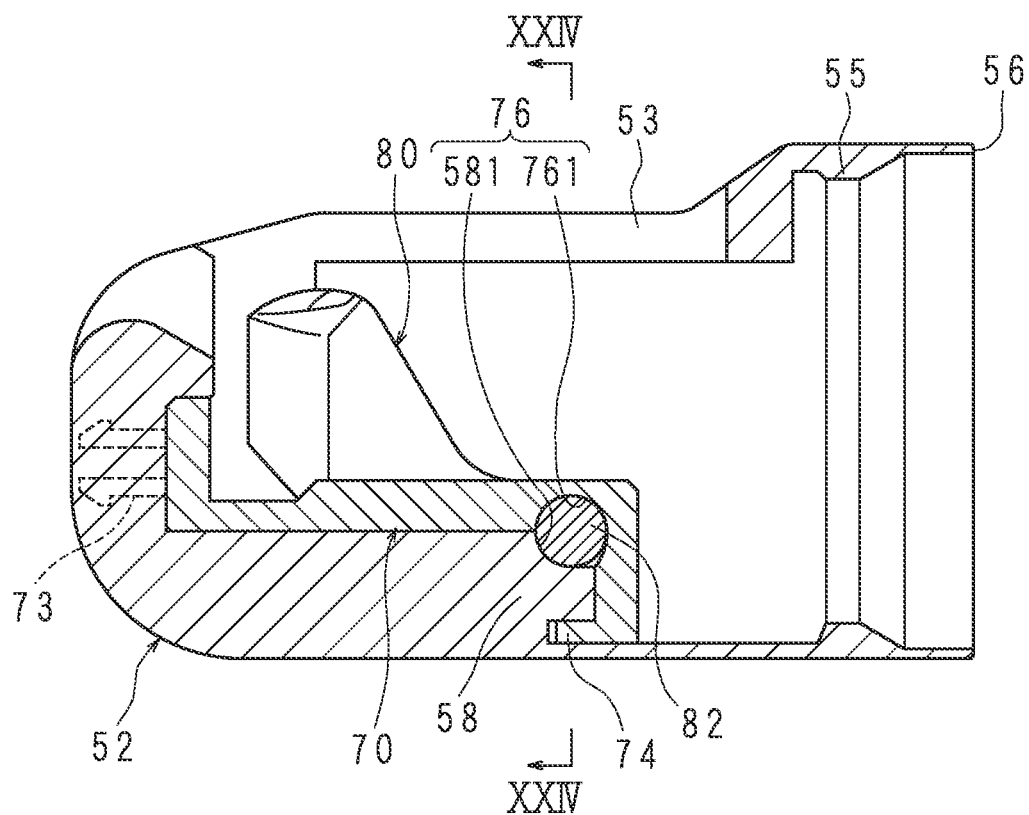
FIG. 23 is a section view of the cap according to Embodiment 3.
Figure 24:
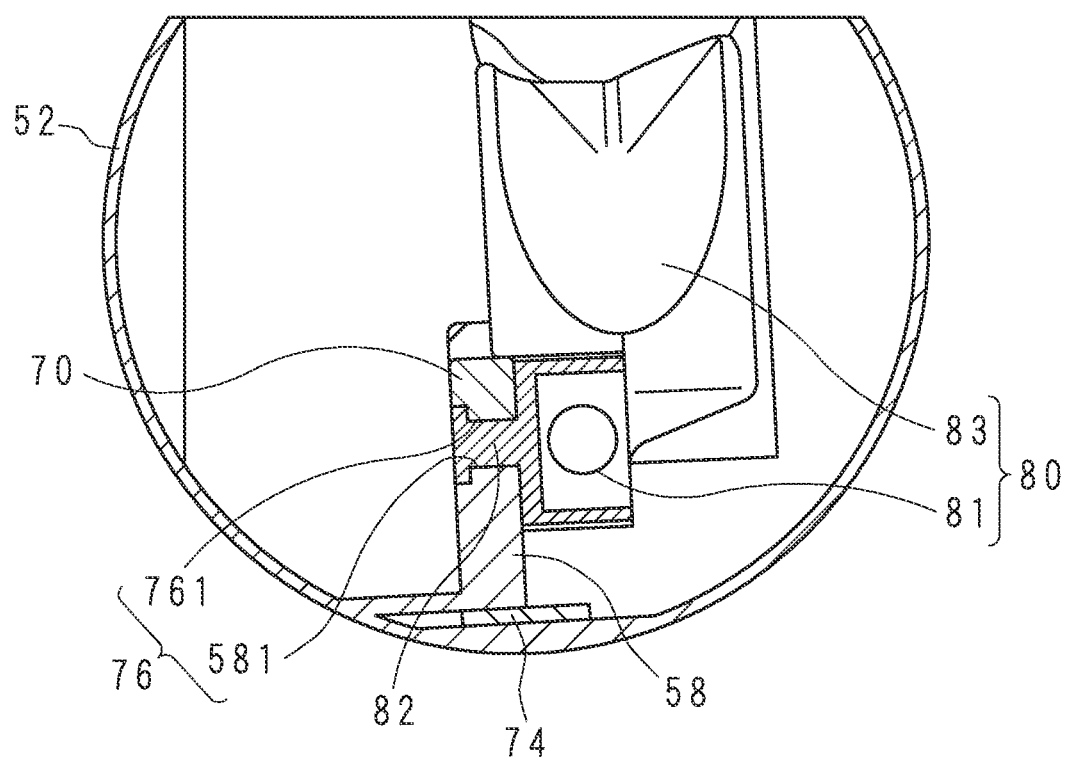
FIG. 24 is a section view of the cap according to Embodiment 3 taken along the line XXIV-XXIV in FIG. 23.

FIG. 20 is an exploded perspective view of the cap 50 according to Embodiment 3. FIG. 21 is a side view of a pedestal 70 and an elevator 80 according to Embodiment 3 combined together. FIG. 22 illustrates the state where a cover 52 and the pedestal 70 according to Embodiment 3 are in the process of being combined together. FIG. 23 is a section view of the cap 50 according to Embodiment 3. FIG. 24 is a section view of the cap 50 according to Embodiment 3 taken along the line XXIV-XXIV in FIG. 23. The configuration of the cap 50 according to the present embodiment will be described with reference to FIGS. 20 to 24.

The cap 50 includes the cover 52, pedestal 70 and elevator 80. The cover 52 has, at the inner surface thereof, a second fixing projection 58 of a substantially L-shaped plate protruding toward the window part 53 and having a tip end further protruding toward the opening end 56. The second fixing projection 58 has, at a corner thereof on the window part 53 side, an elevator receiver 581 which corresponds to approximately one-fourth a cylindrical surface.

The pedestal 70 includes an annular first wall 77 and a rectangular plate-like third wall 79 that are contiguous with each other to form an L shape. At the first wall 77, a first elevator attachment part 761 is formed at an inner surface distant from the third wall 79. The first elevator attachment part 761 corresponds to approximately three quarters of a cylindrical surface that is contiguous with a hole at a middle part of the first wall 77. The first wall 77 is further provided with a plate-like fourth fixing projection 74 protruding toward a third fixing projection 73.

The third wall 79 is provided with the third fixing projection 73 on a surface opposite from the first wall 77. The third fixing projection 73 is a projection having an expanding slot. The third fixing projection 73 has, at an end thereof, a retainer with a diameter one size larger than that of the projection 73.

A method of assembling the cap 50 will now be described. First, the elevator 80 and the pedestal 70 are combined together. More specifically, the elevator shaft 82 is inserted into the hole at the middle part of the first wall 77 so as to abut the inner surface of the first elevator attachment part 761. FIG. 21 illustrates the state where the elevator 80 and the pedestal 70 are combined together. The elevator shaft 82 is temporarily fixed to the inner surface of the first elevator attachment part 761.

Subsequently, the pedestal 70 is fixed to the inner surface of the cover 52. More specifically, the pedestal 70 and the elevator 80 are inserted into the cover 52 through the opening end 56, as illustrated in FIG. 22.

The pedestal 70 is pressed against the bottom of the cover 52. The third fixing projection 73 is engaged into the pedestal fixing hole 57. Here, as illustrated in FIG. 23, the second fixing projection 58 and the fourth fixing projection 74 are engaged with each other. The first elevator attachment part 761 and the elevator receiver 581 together form the elevator attachment hole 76 having a cylindrical surface surrounding the elevator shaft 82. The elevator attachment hole 76 pivotally supports the elevator shaft 82. The procedures described above complete the cap 50.

As illustrated in FIG. 20, the direction of inserting the elevator shaft 82 into the hole of the first wall 77 intersects with the direction of inserting the pedestal 70 into the cover 52.

According to the present embodiment, the cap 50 in which the elevator shaft 82 and the pedestal 70 are easily assembled may be provided. Furthermore, since the pedestal 70 is fixed to the inner surface of the cover 52 with the plate-like fourth fixing projection 74, it is possible to provide the cap 50 in which the pedestal 70 is not likely to come off the cover 52 even if a force of pulling the pedestal 70 and the elevator 80 in the direction of the window part 53 is applied.

Embodiment 4

The present embodiment relates to a cap 50 having a fixing projection for fixing a pedestal 70 to the bottom of a cover 52. Portions common to those in Embodiment 3 will not be described here.

Figure 25:
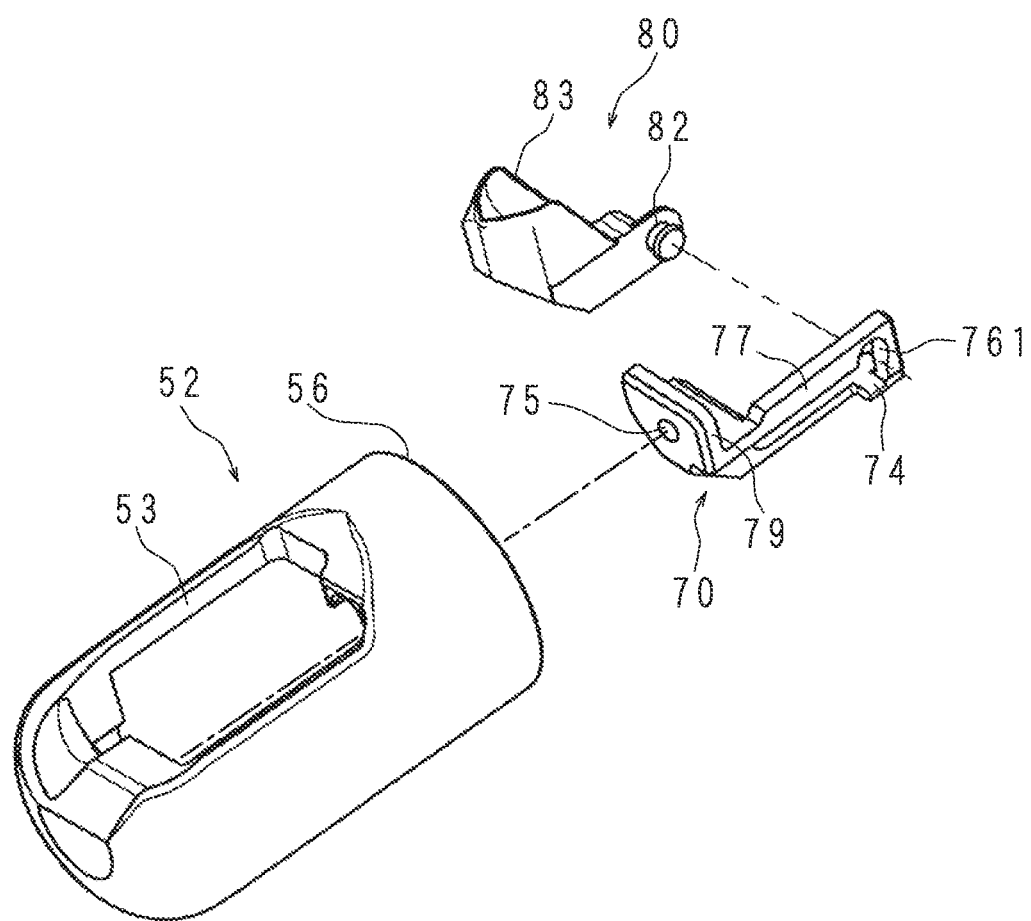
FIG. 25 is an exploded perspective view of a cap according to Embodiment 4.
Figure 26:
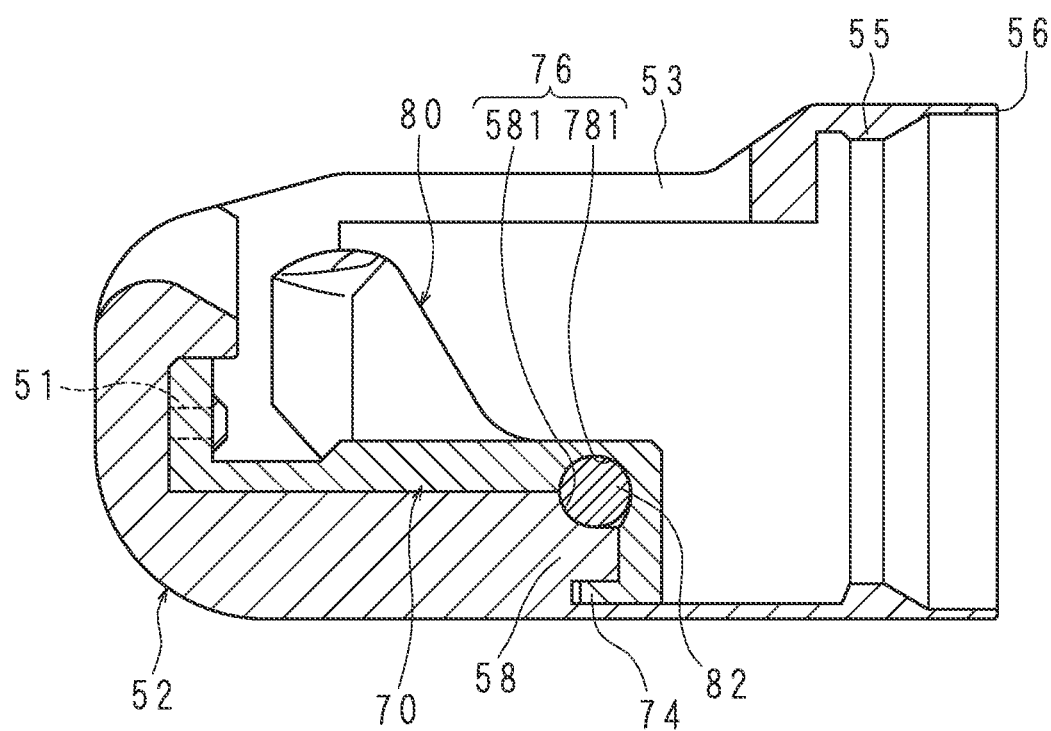
FIG. 26 is a section view of the cap according to Embodiment 4.

FIG. 25 is an exploded perspective view of the cap 50 according to Embodiment 4. FIG. 26 is a section view of the cap 50 according to Embodiment 4. The configuration of the cap 50 according to the present embodiment will be described with reference to FIGS. 25 and 26.

The cap 50 has a cover 52, a pedestal 70 and an elevator 80. The cover 52 has, at the bottom thereof, a fifth fixing projection 51 protruding toward the opening end. The fifth fixing projection 51 has, at an end thereof, a retainer with a diameter one size larger than that of the projection 51. The pedestal 70 has a cover fixing hole 75 penetrating through the third wall 79.

By pressing the pedestal 70 against the bottom of the cover 52, the fifth fixing projection 51 is engaged into the cover fixing hole 75.

According to the present embodiment, the cap 50 having a smooth bottom, i.e. a smooth portion that is in contact with the distal end of the insertion part 30 when attached to the endoscope 10, may be provided.

Embodiment 5

The present embodiment relates to an endoscope 10 that provides a feel of click when a cap 50 is attached to a distal end portion 31. Portions common to those in Embodiment 1 will not be described here.

Figure 27:
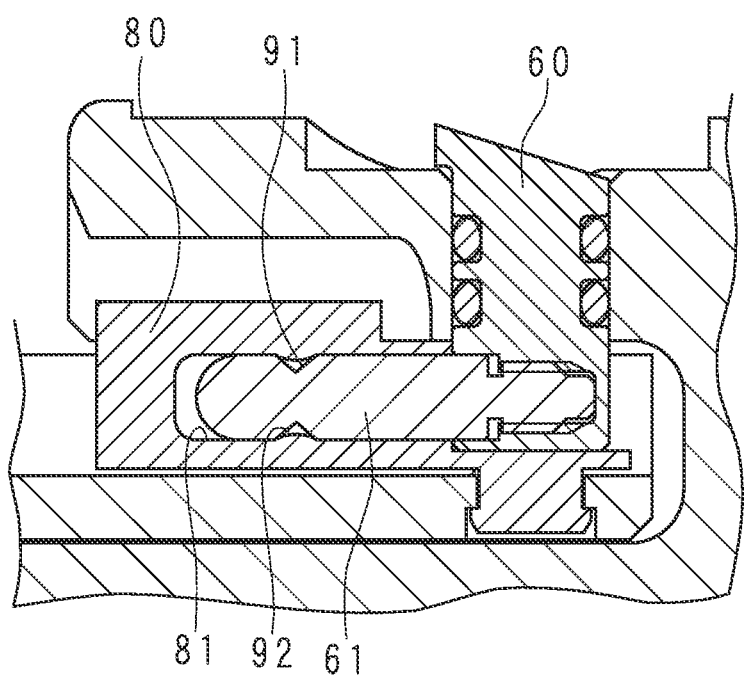
FIG. 27 is a section view of a portion where a lever and an elevator according to Embodiment 5 are connected with each other.

FIG. 27 is a section view of a portion where a lever 60 and an elevator 80 according to Embodiment 5 are connected with each other. A side surface concave part 91 having the shape of a triangular groove is formed at the outer periphery of the elevator connection part 61 protruding from the lever 60. An inner surface convex part 92 having the shape corresponding to the side surface concave part 91 is formed at the inner periphery of the concave lever connection part 81 located at the elevator 80. In the state where the lever 60 and the elevator 80 are connected with each other, the inner surface convex part 92 fits into the side surface concave part 91 as illustrated in FIG. 27.

When the cap 50 is attached to the distal end portion 31, the elevator connection part 61 thrusts into the lever connection part 81 while pushing out the inner surface convex part 92. When the inner surface convex part 92 fits into the side surface concave part 91, the user who is working to attach the cap 50 may sense a feel of click. Thus, the user may recognize that the cap 50 is pushed to reach a predetermined position.

According to the present embodiment, the endoscope 10 that provides a feel of click when the cap 50 is pushed to a predetermined position of the distal end portion 31 may be provided.

It is also possible to form a convex part at the outer periphery of the elevator connection part 61 and a concave part at the inner periphery of the lever connection part 81.

Embodiment 6

The present embodiment relates to a cap 50 in which a pedestal 70 and a cover 52 are formed in an integral manner. Portions common to those in Embodiment 1 will not be described here.

Figure 28:
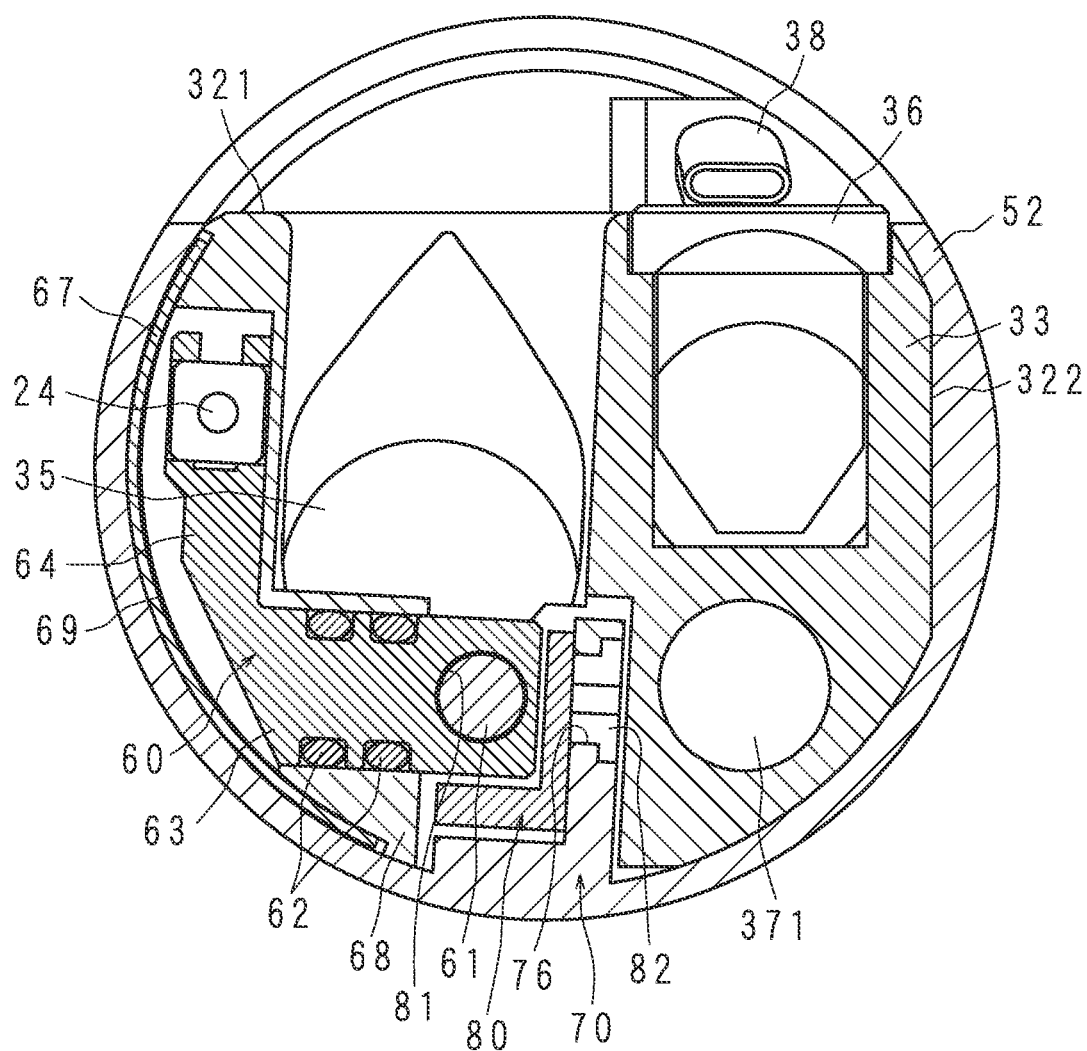
FIG. 28 is a section view of an insertion part according to Embodiment 6.

FIG. 28 is a section view of an insertion part 30 according to Embodiment 6. FIG. 28 illustrates a cross section cut at a position similar to the line XI-XI indicated in FIG. 10. In the present embodiment, the pedestal 70 is integrally formed with the inner surface of the cover 52.

For example, a 3D printer may be used to fabricate the cover 52 of this type. The use of the 3D printer capable of printing more than one materials allows for simultaneous fabrication of the pedestal 70 and cover 52, as well as the elevator 80 which can pivot with respect to the pedestal 70.

According to the present embodiment, it is possible to provide the cap 50 with a small number of components to be used.

Embodiment 7

The present embodiment relates to an endoscope 10 including a lever connection part 81 of a projection shape and an elevator connection part 61 of a concave shape. Portions common to those in Embodiment 1 will not be described here.

Figure 29:
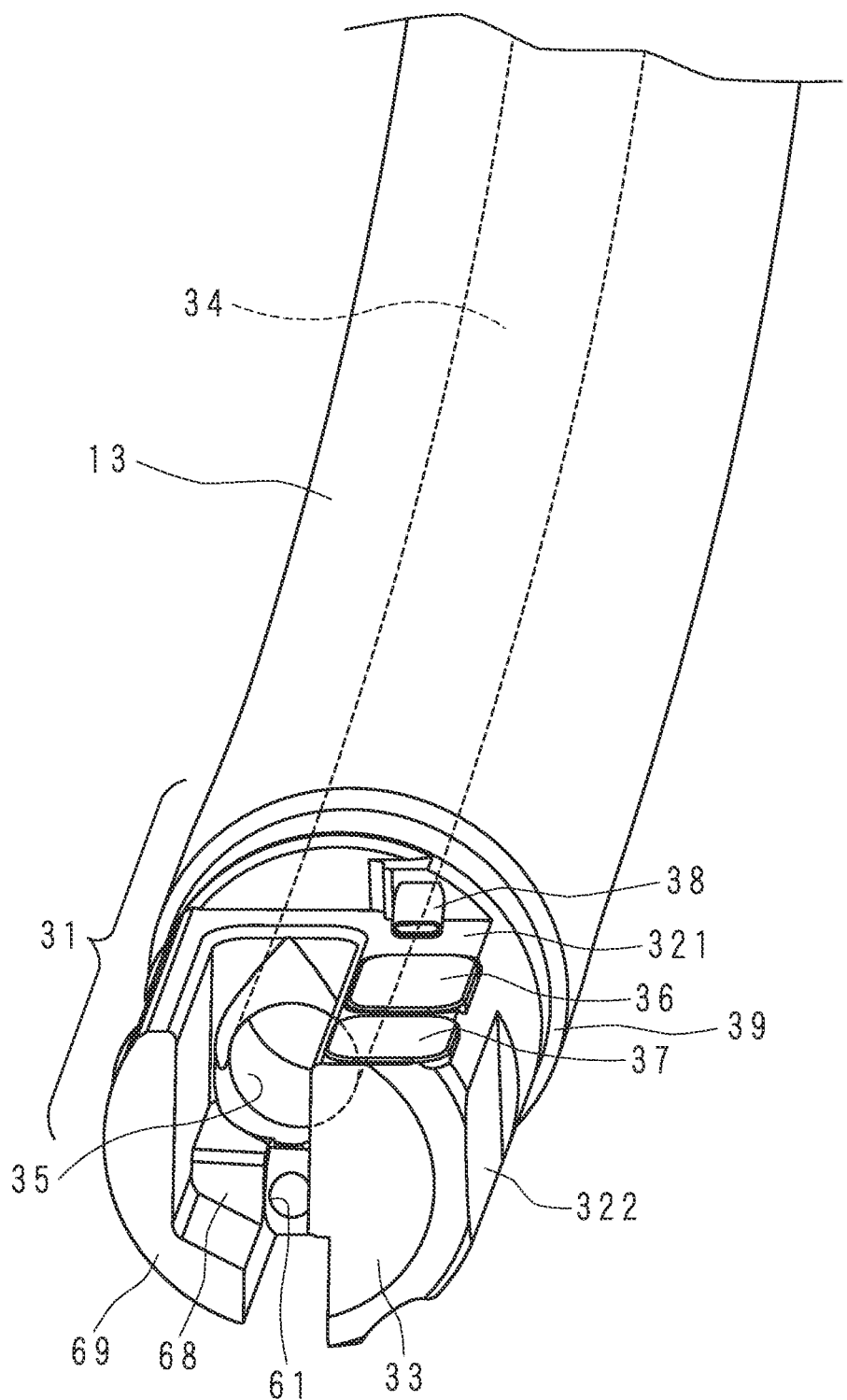
FIG. 29 is a perspective view of a distal end of an insertion part according to Embodiment 7 before a cap is attached.
Figure 30:
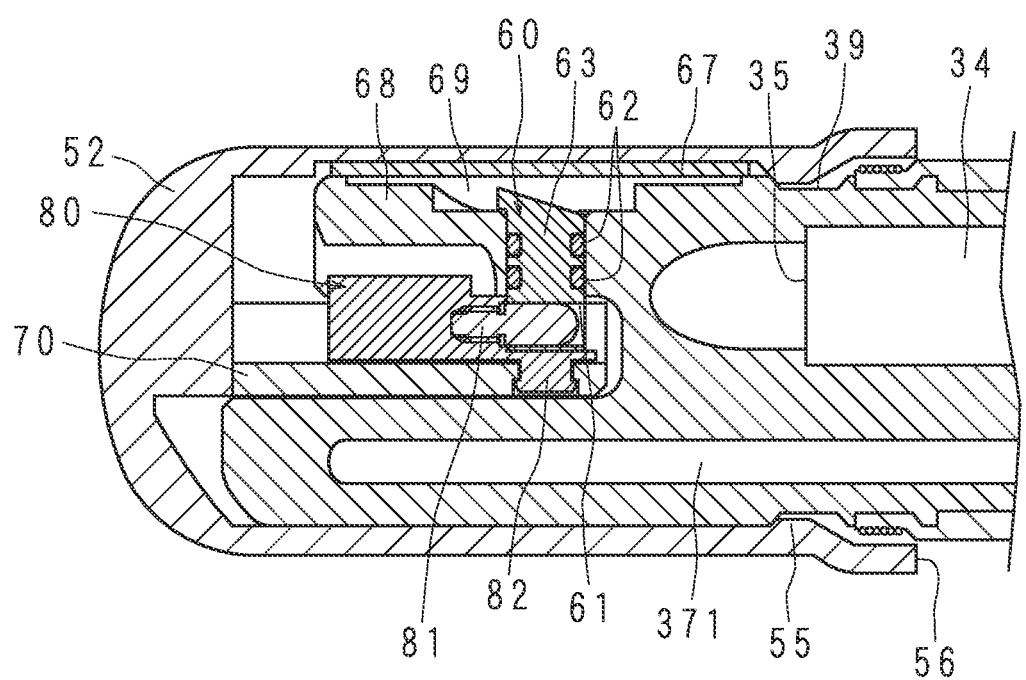
FIG. 30 is a section view of the insertion part according to Embodiment 7.
Figure 31:
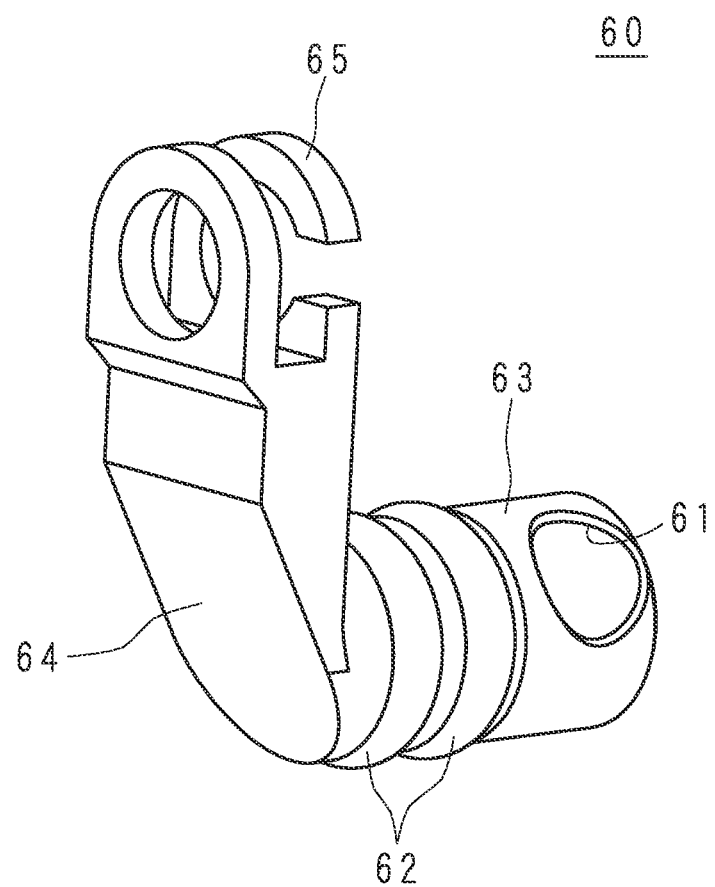
FIG. 31 is a perspective view of a lever according to Embodiment 7.
Figure 32:
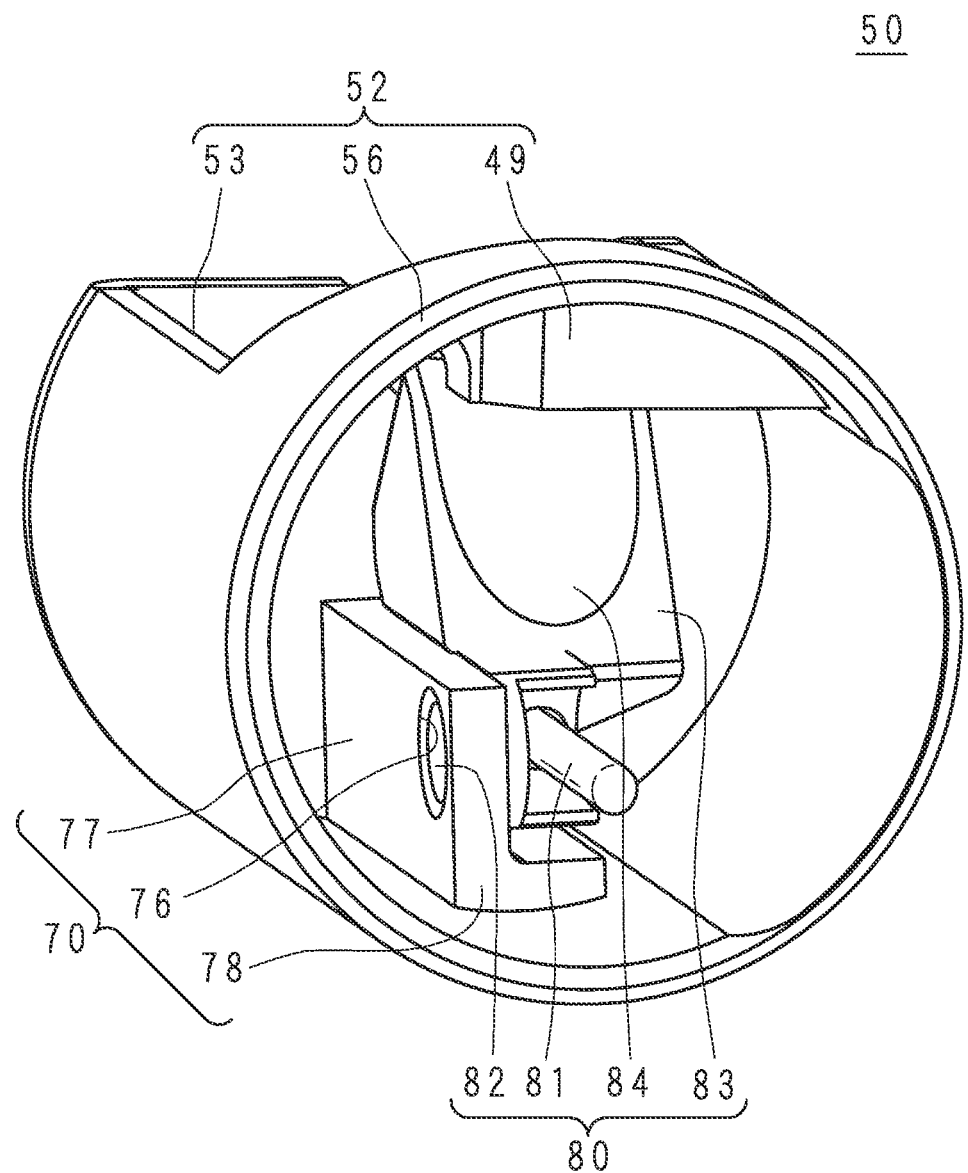
FIG. 32 is a perspective view of a cap according to Embodiment 7.

FIG. 29 is a perspective view of a distal end of an insertion part 30 according to Embodiment 7 before a cap 50 is attached. FIG. 30 is a section view of an insertion part 30 according to Embodiment 7. FIG. 31 is a perspective view of a lever 60 according to Embodiment 7. FIG. 32 is a perspective view of the cap 50 according to Embodiment 7. The structure of the endoscope 10 according to the present embodiment will be described with reference to FIGS. 29 to 32.

As illustrated in FIGS. 29 and 31, the elevator connection part 61 according to the present embodiment is a round hole formed at a side surface of a lever shaft 63. For the elevator connection part 61, a hole of any shape such as a rectangular hole or an elliptical hole may be employed. The elevator connection part 61 may or may not penetrate through the lever shaft 63. In the following description, the elevator connection part 61 having the shape of a recess as illustrated in FIG. 30 may also be referred to as a connection concave part.

As illustrated in FIG. 32, the lever connection part 81 according to the present embodiment is a columnar projection formed on the inner surface of the cylindrical surface that is coaxial with the elevator shaft 82 so as to intersect the elevator shaft 82. In the following description, the lever connection part 81 having the shape of a projection as illustrated in FIG. 31 may also be referred to as an elevator projection. The lever connection part 81 has a shape which may be inserted into the elevator connection part 61 formed at the lever 60.

FIG. 30 is a cross section passing the central axis of the lever shaft 63 and the central axis of the elevator shaft 82 along the longitudinal direction of the insertion part 30. The lever connection part 81 is inserted into the elevator connection part 61.

According to the present embodiment, the distal end of the insertion part 30 only has a hole of the elevator connection part 61, which facilitates cleaning after use. It is noted that a brush corresponding to the dimension of the elevator connection part 61 is used to clean the inside of the elevator connection part 61.

Embodiment 8

The present embodiment relates to an endoscope 10 in which a lever shaft 63 also serves as an elevator projection. Portions common to those in Embodiment 1 will not be described here.

Figure 33:
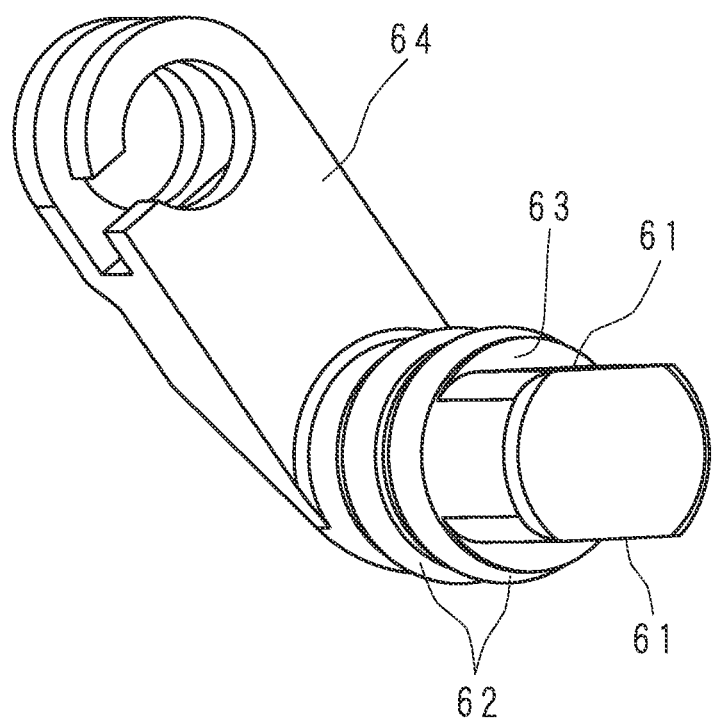
FIG. 33 is a perspective view of a lever according to Embodiment 8.
Figure 34:
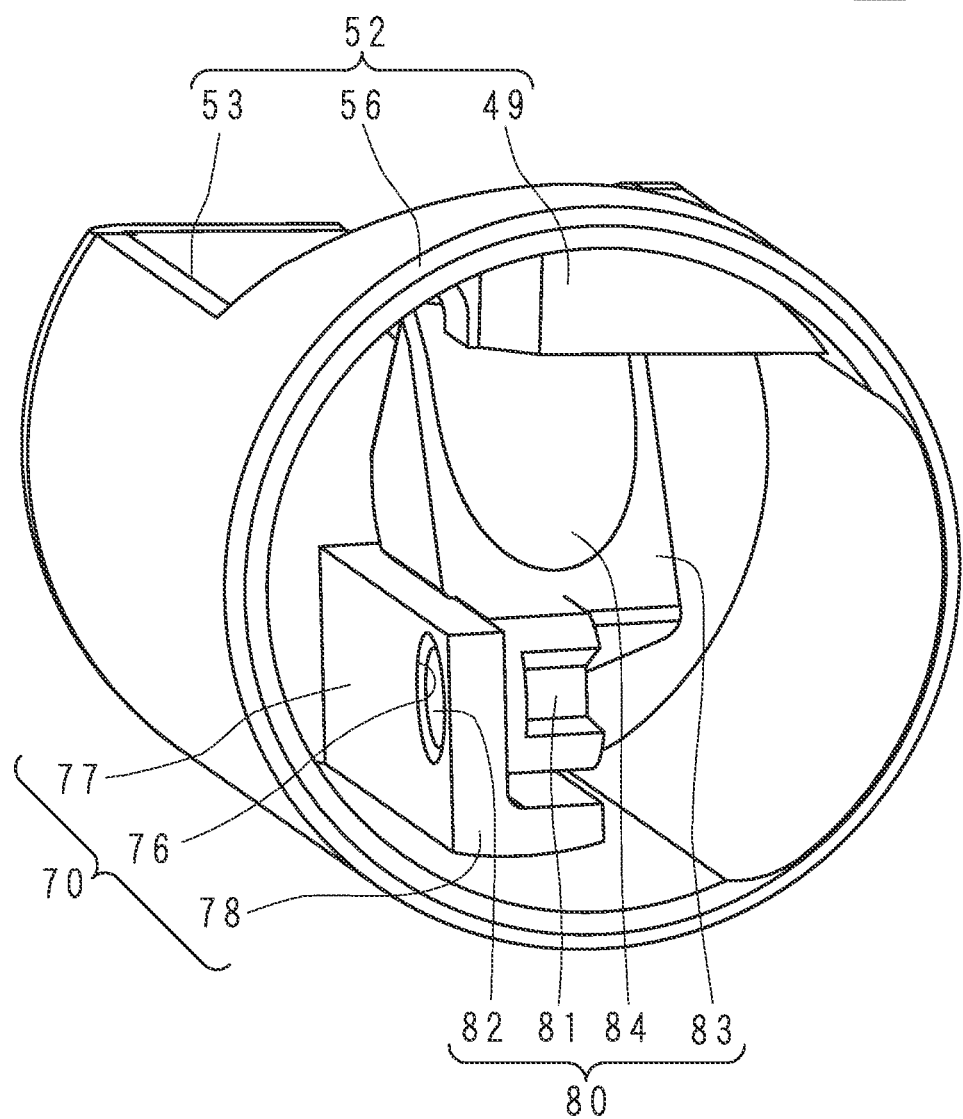
FIG. 34 is a perspective view of a cap according to Embodiment 8.

FIG. 33 is a perspective view of a lever 60 according to Embodiment 8. FIG. 34 is a perspective view of a cap 50 according to Embodiment 8. The configuration of the endoscope 10 according to the present embodiment will be described with reference to FIGS. 33 and 34.

As illustrated in FIG. 33, the lever shaft 63 according to the present embodiment has two cutouts in a direction parallel to the central axis, and includes two parallel planar elevator connection parts 61. As illustrated in FIG. 34, the lever connection part 81 according to the present embodiment is a substantially U-shaped recess formed at a side surface of a columnar surface that is coaxial with the elevator shaft 82 so as to intersect with the elevator shaft 82.

The cap 50 is pushed onto the insertion part 30 from its distal end so that the elevator connection part 61 fits into the lever connection part 81. This connects the lever 60 and the elevator 80 with each other so that they may able to pivot in an integrated manner. That is, in the present embodiment, the lever shaft 63 also serves as an elevator projection.

According to the present embodiment, the distal end of the insertion part 30 has neither a projection nor a hole, which facilitates cleaning after use.

Only one of the elevator connection parts 61 may be provided. The two elevator connection parts 61 may not necessarily be parallel to each other.

Embodiment 9

The present embodiment relates to an endoscope 10 in which a member for connecting a lever 60 and an elevator 80 is detachable. Portions common to those in Embodiment 1 will not be described here.

Figure 35:
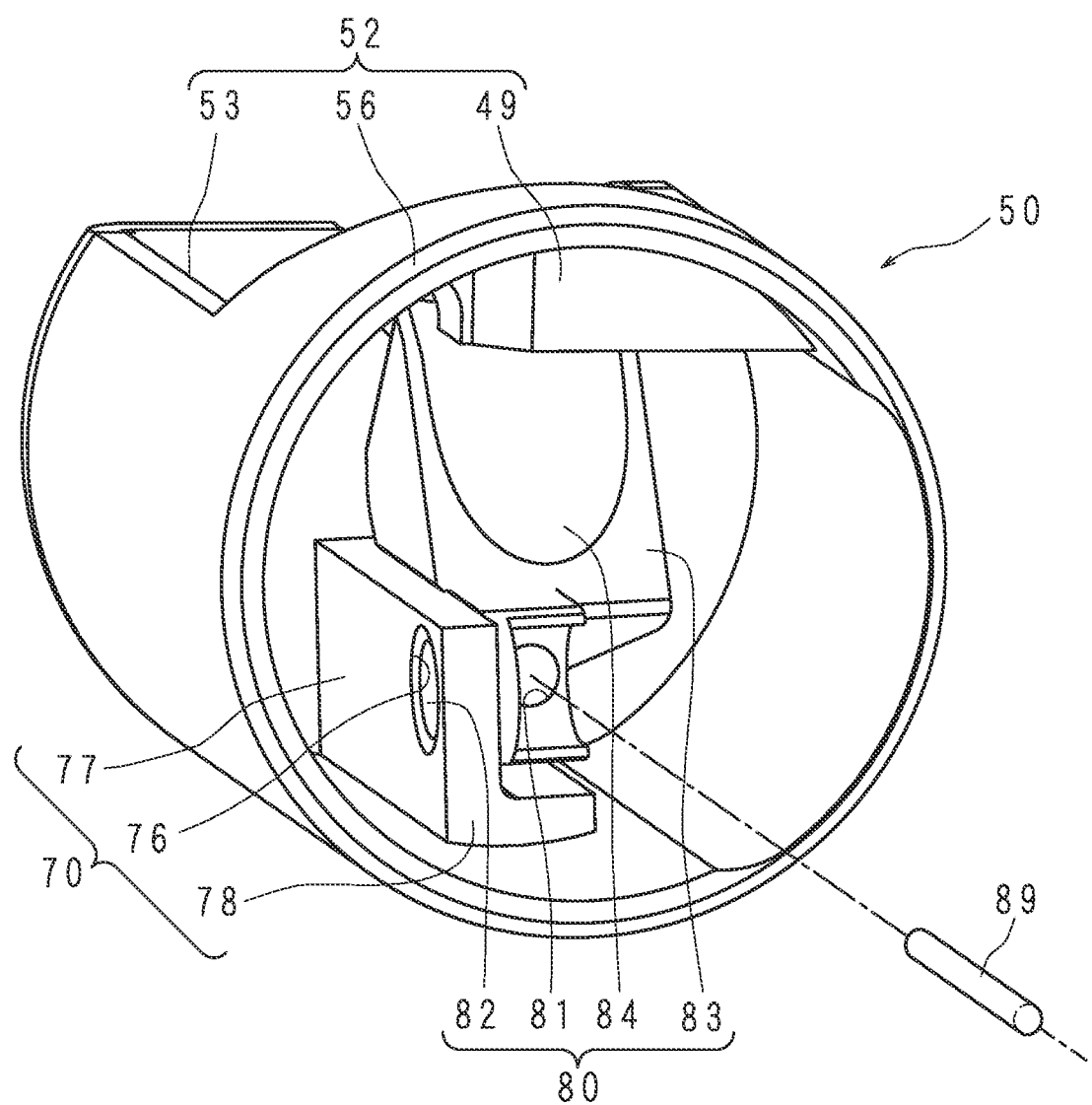
FIG. 35 is a perspective view of a cap according to Embodiment 9.

FIG. 35 is a perspective view of a cap 50 according to Embodiment 9. The cap 50 according to the present embodiment has a recessed lever connection part 81 as in Embodiment 1 described with reference to FIG. 4. The endoscope 10 according to the present embodiment has a recessed elevator connection part 61 at the distal end of the insertion part 30, as in Embodiment 6 described with reference to FIGS. 29 and 30. The endoscope 10 according to the present embodiment comprises a round bar-like connecting tool 89.

After the connecting tool 89 is inserted into the lever connection part 81 or elevator connection part 61, the cap 50 is pushed onto the insertion part 30 and fixed. The connecting tool 89 fits into the elevator connection part 61 and the lever connection part 81. This allows the lever 60 and the elevator 80 to pivot in an integrated manner.

According to the present embodiment, the distal end of the insertion part 30 only has a hole of the elevator connection part 61, which facilitates cleaning after use. Moreover, the connecting tool 89 may easily be cleaned and reused because of its simple shape. Thus, the endoscope 10 with a small number of members to be discarded even if the cap 50 is made as single use may be provided.

The lever connection part 81 may be a prism, elliptical column or the like. Magnetic substances are used for the lever 60, elevator 80 and connecting tool 89, so that the endoscope 10 may be provided which prevents the components from falling off at the time of attachment and facilitates the attachment of the cap 50.

Embodiment 10

The present embodiment relates to an endoscope 10 which may obtain a feel of click when the cap 50 is attached to the distal end portion 31. Portions common to those in Embodiment 1 will not be described here.

Figure 36:
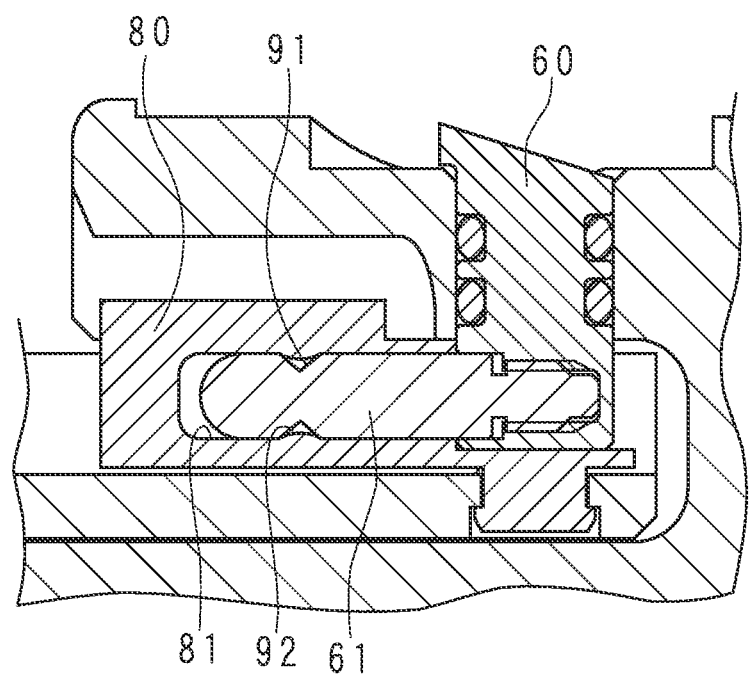
FIG. 36 is a section view of a portion where a lever and an elevator according to Embodiment 10 are connected with each other.

FIG. 36 is a section view of a portion where a lever 60 and an elevator 80 according to Embodiment 10 are connected with each other. A side surface concave part 91 having the shape of a triangular groove is formed at the outer periphery of the elevator connection part 61 protruding from the lever 60. An inner surface convex part 92 having the shape corresponding to the side surface concave part 91 is formed at the inner periphery of the concave lever connection part 81 located at the elevator 80. In the state where the lever 60 and the elevator 80 are connected with each other, the inner surface convex part 92 fits into the side surface concave part 91 as illustrated in FIG. 36.

When the cap 50 is attached to the distal end portion 31, the elevator connection part 61 thrusts into the lever connection part 81 while pushing out the inner surface convex part 92. While the inner surface convex part 92 thrusts into the side surface concave part 91, the user who is working to attach the cap 50 may sense a feel of click. Thus, the user may recognize that the cap 50 is pushed to reach a predetermined position.

According to the present embodiment, the endoscope 10 producing a feel of click when the cap 50 is pushed to a predetermined position of the distal end portion 31 may be provided.

Embodiment 11

The present embodiment relates to an endoscope 10 which may obtain a feel of click when the cap 50 is attached to the distal end portion 31. Portions common to those in Embodiment 7 will not be described here.

Figure 37:
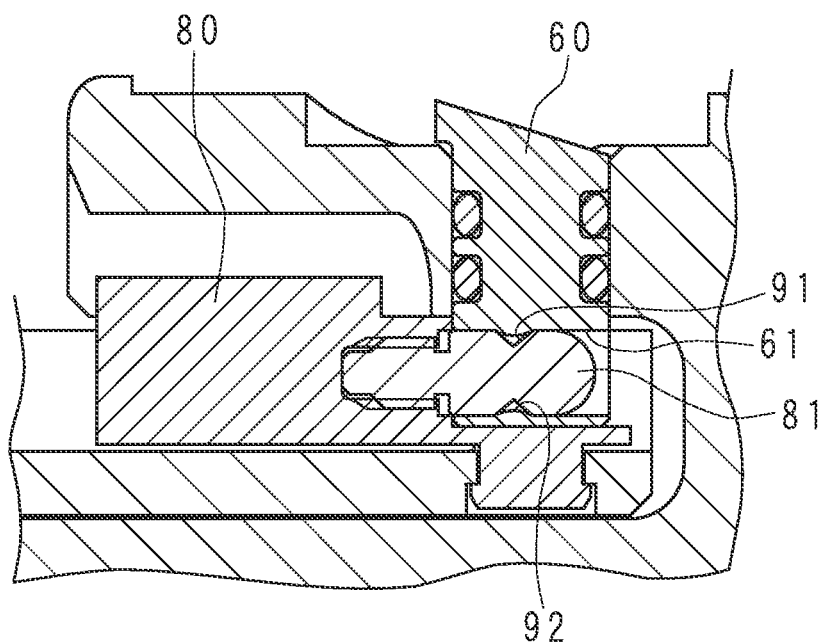
FIG. 37 is a section view of a portion where a lever and an elevator according to Embodiment 11 are connected with each other.

FIG. 37 is a section view of a portion at which a lever 60 and an elevator 80 according to Embodiment 11 are connected with each other. A side surface concave part 91 having the shape of a triangular groove is formed at the outer periphery of the lever connection part 81 protruding from the elevator 80. An inner surface convex part 92 having the shape corresponding to the side surface concave part 91 is formed at the inner periphery of the concave elevator connection part 61 located at the lever 60. In the state where the lever 60 and the elevator 80 are connected with each other, the inner surface convex part 92 fits into the side surface concave part 91 as illustrated in FIG. 37.

When the cap 50 is attached to the distal end portion 31, the lever connection part 81 thrusts into the elevator connection part 61 while pushing out the inner surface convex part 92. When the inner surface convex part 92 thrusts into the side surface concave part 91, the user who is working to attach the cap 50 may sense a feel of click. Thus, the user may recognize that the cap 50 is pushed to reach a predetermined position.

According to the present embodiment, the endoscope 10 producing a feel of click when the cap 50 is pushed to reach a predetermined position of the distal end portion 31 may be provided.

The technical features (components) described in each example embodiment may be combined with one another, and such combinations may form new technical features.

It is to be noted that, as used herein and in the appended claims, the singular forms "a", "an", and "the" include plural referents unless the context clearly dictates otherwise.

It should be understood that the embodiments disclosed herein are illustrative and non-restrictive in every respect. Since the scope of the present invention is defined by the appended claims rather than by the description preceding them, all changes that fall within metes and bounds of the claims, or equivalence of such metes and bounds thereof are therefore intended to be embraced by the claims.

In relation to the embodiments including Embodiments 1 to 11 described above, the following clauses will further be disclosed.

1. An endoscope cap attachable to and detachable from an endoscope including a lever pivotally provided at a distal end of an insertion part of an endoscope and a pivot part causing the lever to pivot, comprising:
  a bottomed cylindrical cover having an opening end; and
  an elevator pivotally supported at an inside of the cover, connected to the lever when the cover is attached to the endoscope, and pivoting in response to pivoting of the lever.

2. The endoscope cap according to clause 1, wherein the cover has a window part at a side surface, and the elevator includes an elevator shaft pivotally supported by the cover and a lever connection part located at the opening end side and connectable to the lever.

3. The endoscope cap according to clause 2, wherein the elevator is pivotable in a direction of changing a distance between the elevator and the window part.

4. The endoscope cap according to clause 2 or 3, wherein the cover has a cutout contiguous to the window part.

5. The endoscope cap according to any one of clauses 2 to 4, further comprising a pedestal fixed to an inside of the cover,
  wherein the elevator shaft is pivotally supported at the inner side of the cover through the pedestal.

6. An endoscope, comprising:
  a hollow lever chamber protruding from a part of a distal end of an insertion part in an insertion direction and including a support wall along the insertion direction; and
  a lever having a lever shaft penetrating the support wall and an elevator connection part located outside the lever chamber and exposed to a surface, the lever being pivotable around the lever shaft.

7. The endoscope according to clause 6, comprising an endoscope cap including:
  a bottomed cylindrical cover having an opening end; and
  an elevator pivotally supported at an inner side of the cover, connected to the lever when the cover is attached to the endoscope, and pivoting in response to pivoting of the lever.

8. A method of manufacturing an endoscope cap, comprising:
  inserting an elevator shaft of an elevator into a pedestal;
  inserting the pedestal together with the elevator into a bottomed cylindrical cover having an opening end through the opening end; and
  fixing the cover and the pedestal to each other.

9. A method of using an endoscope cap, comprising:
  preparing an endoscope including a lever pivotally provided at a distal end of an insertion part of an endoscope and a pivot part pivoting the lever; and
  attaching an endoscope cap to the endoscope, the endoscope cap including: a bottomed cylindrical cover having an opening end; and an elevator pivotally supported at an inner side of the cover, connected to the lever when the cover is attached to the endoscope, and pivoting in response to pivoting of the lever.

10. A method of using the endoscope cap according to clause 9, comprising:
  breaking the cover through a cutout formed at the cover; and
  removing the endoscope cap from the endoscope after breaking.

What is claimed is:

1. An endoscope cap comprising:
  a cover having an opening end and having a bottomed cylindrical shape which makes the opening end attachable to and detachable from a distal end of an insertion part of an endoscope and having a first fixing projection provided on an internal surface of a cylindrical part in an axial direction of the cylindrical part;
  a pedestal formed separately from the cover and having a first wall and a second wall, the second wall being a rectangular plate attached to an internal surface of the cover, the first wall rising from one of long sides of the second wall and being penetrated by an elevator attachment hole, the second wall having a pedestal edge projection that projects along one of long sides of a surface opposite to a surface on which the first wall rises, the pedestal edge projection being disposed so as to abut against the first fixing projection;

an elevator located inside the cover and having an elevator shaft inserted into the elevator attachment hole, an elevating part protruding in a direction intersecting the elevator shaft, and a connection concave part being opened at an opening end side of the elevating part and connected to a lever provided at the endoscope, the elevator being pivotable around the elevator shaft with respect to the pedestal; and wherein the cover includes two of the first fixing projections projecting in a direction facing each other, the pedestal includes two of the pedestal edge projections projecting along both of the long sides of the second wall, and the pedestal edge projections are respectively engaged with the first fixing projections.

2. The endoscope cap according to claim 1, wherein the two of the first fixing projections are disposed in parallel with each other.

3. An endoscope cap comprising:

a cover having an opening end and having a bottomed cylindrical shape which makes the opening end attachable to and detachable from a distal end of an insertion part of an endoscope and having a first fixing projection provided on an internal surface of a cylindrical part in an axial direction of the cylindrical part;

a pedestal formed separately from the cover and having a first wall and a second wall, the second wall being a rectangular plate attached to an internal surface of the cover, the first wall rising from one of long sides of the second wall and being penetrated by an elevator attachment hole, the second wall having a pedestal edge projection that projects along one of long sides of a surface opposite to a surface on which the first wall rises, the pedestal edge projection being disposed so as to abut against the first fixing projection;

an elevator located inside the cover and having an elevator shaft inserted into the elevator attachment hole, an elevating part protruding in a direction intersecting the elevator shaft, and a connection concave part being opened at an opening end side of the elevating part and connected to a lever provided at the endoscope, the elevator being pivotable around the elevator shaft with respect to the pedestal;

wherein the cover includes a pedestal fixing hole at a bottom, and the pedestal has a third wall rising in a same direction as the first wall from a short side of the second wall on a bottom side of the cover, and a third fixing projection projecting on a surface opposite to the first wall of the third wall and penetrating the pedestal fixing hole.

4. The endoscope cap according to claim 3, wherein the third fixing projection has a retainer at its end.

5. The endoscope cap according to claim 3, wherein the third fixing projection has an expanding slot at its end.

* * * * *